US010506989B2

(12) United States Patent
Maruo

(10) Patent No.: US 10,506,989 B2
(45) Date of Patent: Dec. 17, 2019

(54) METHOD FOR QUANTIFYING GLUCOSE CONCENTRATION AND GLUCOSE CONCENTRATION MEASUREMENT DEVICE

(71) Applicant: PHC Holdings Corporation, Minato-ku, Tokyo (JP)

(72) Inventor: Katsuhiko Maruo, Hyogo (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 471 days.

(21) Appl. No.: 15/304,064

(22) PCT Filed: Sep. 4, 2015

(86) PCT No.: PCT/JP2015/075189
§ 371 (c)(1),
(2) Date: Oct. 14, 2016

(87) PCT Pub. No.: WO2016/035881
PCT Pub. Date: Mar. 10, 2016

(65) Prior Publication Data
US 2017/0027526 A1 Feb. 2, 2017

(30) Foreign Application Priority Data
Sep. 5, 2014 (JP) .................. 2014-181283

(51) Int. Cl.
*A61B 5/1455* (2006.01)
*A61B 5/00* (2006.01)
*A61B 5/145* (2006.01)

(52) U.S. Cl.
CPC .......... *A61B 5/7278* (2013.01); *A61B 5/1455* (2013.01); *A61B 5/14532* (2013.01)

(58) Field of Classification Search
CPC . A61B 5/7278; A61B 5/14532; A61B 5/1455; A61B 5/14551; G01N 21/359; G01N 2201/12
See application file for complete search history.

(56) References Cited

U.S. PATENT DOCUMENTS 5,747,806 A 5/1998 Khalil et al.
5,945,676 A 8/1999 Khalil et al.
(Continued)

FOREIGN PATENT DOCUMENTS

JP  H08-235242 A  9/1996
JP  H11-506207 A  6/1999
(Continued)

OTHER PUBLICATIONS

Internationanl Search Report of corresponding PCT Application No. PCT/JP2015/075189 dated Nov. 17, 2015.
(Continued)

*Primary Examiner* — Eric F Winakur
*Assistant Examiner* — Chu Chuan Liu
(74) *Attorney, Agent, or Firm* — Wenderoth, Lind & Ponack, L.L.P.

(57) ABSTRACT

A method for quantifying a glucose concentration is a method for quantifying a glucose concentration in which near-infrared light is emitted onto a living organism and a glucose concentration in a biological tissue is measured using a signal obtained by receiving diffusely reflected light or transmitted light from the biological tissue. A concentration calculation step calculates a concentration index of a glucose component by using at least a spectrum of a water component, a spectrum of a glucose component, and a spectrum of a fat component to synthesize a difference spectrum between a measurement spectrum at a time of measurement of a glucose concentration and a spectrum
(Continued)

serving as a reference obtained previous to the measurement spectrum. A glucose concentration calculation step calculates a glucose concentration in the living organism using the calculated concentration index.

14 Claims, 26 Drawing Sheets

(56) References Cited

U.S. PATENT DOCUMENTS

| | | | |
|---|---|---|---|
| 6,687,620 | B1* | 2/2004 | Haaland ............... G01N 21/274 |
| | | | 702/22 |
| 9,370,323 | B2 | 6/2016 | Amano et al. |
| 2004/0127777 | A1 | 7/2004 | Ruchti et al. |
| 2012/0101347 | A1* | 4/2012 | Amano ............... A61B 5/14532 |
| | | | 600/316 |
| 2012/0166092 | A1 | 6/2012 | Maruo |
| 2015/0045636 | A1* | 2/2015 | Novotny ................. G01J 3/42 |
| | | | 600/316 |

FOREIGN PATENT DOCUMENTS

| | | |
|---|---|---|
| JP | 2004-261364 A | 9/2004 |
| JP | 2006-512931 A | 4/2006 |
| JP | 2008-049091 A | 3/2008 |
| JP | 2011-062335 A | 3/2011 |
| JP | 2012-021811 A | 2/2012 |
| JP | 2012-85877 | 5/2012 |
| JP | 2014-018478 A | 2/2014 |
| JP | 2014-183971 A | 10/2014 |
| JP | 6116956 | 4/2017 |
| WO | 97/28438 A1 | 8/1997 |
| WO | 03/063699 A1 | 8/2003 |
| WO | 2011/013694 A1 | 2/2011 |

OTHER PUBLICATIONS

Katsuhiko Maruo, et al., New Methodology to Obtain a Calibration Model for Noninvasive Near-Infrared Blood Glucose Monitoring, Applied Spectroscopy, Apr. 2006, vol. 60, No. 4, pp. 441-449.
Katsuhiko Maruo, Featured Articles Light and Medical Care, Blood Glucose Monitoring by Near Infrared Spectroscopy: Noninvasive Blood Glucose Level Measurement Using Light Propagation Simulation, Optical alliance, Mar. 1, 2009 (Mar. 1, 2009), vol. 20, No. 3, pp. 20-23.
Tokyo Kagaku-Dojin "Fundamental Principles and Practical Use of FT-IR Spectroscopy, Second Edition" (1994) Editor: Mitsuo Tasumi.
Office Action from the corresponding Japanese Patent Application No. 2013-060697 dated Dec. 20, 2016.
Notice of Allowance from the corresponding Japanese Patent Application No. 2013-060697 dated Mar. 7, 2017.

* cited by examiner (a)
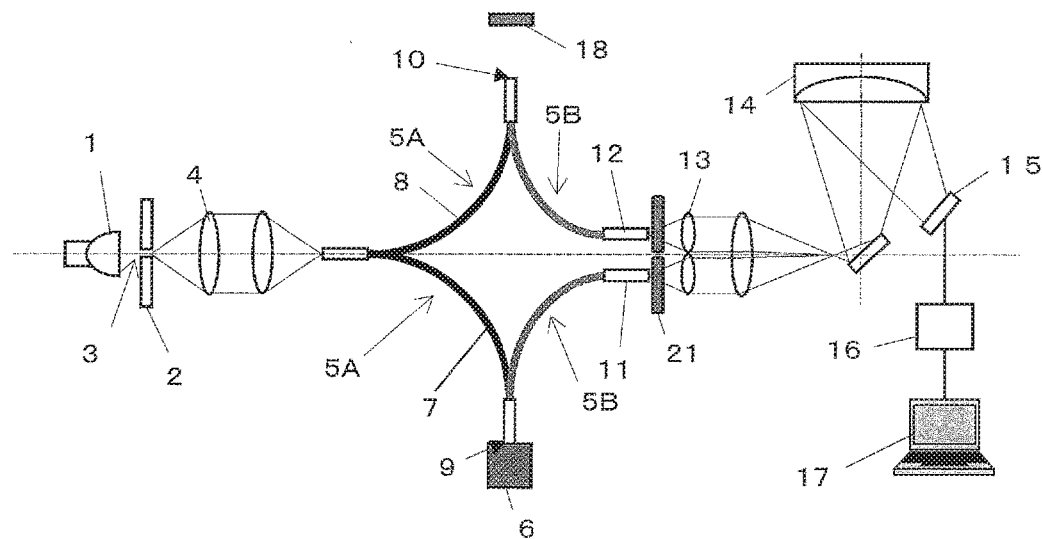
(b)
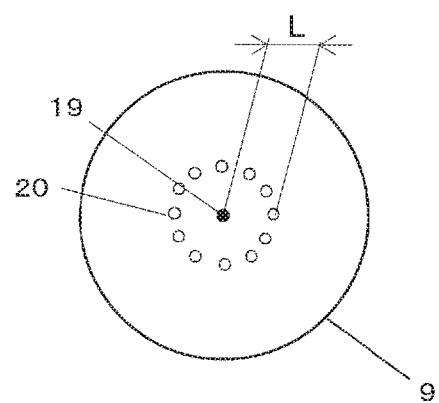
FIG. 1

(a) 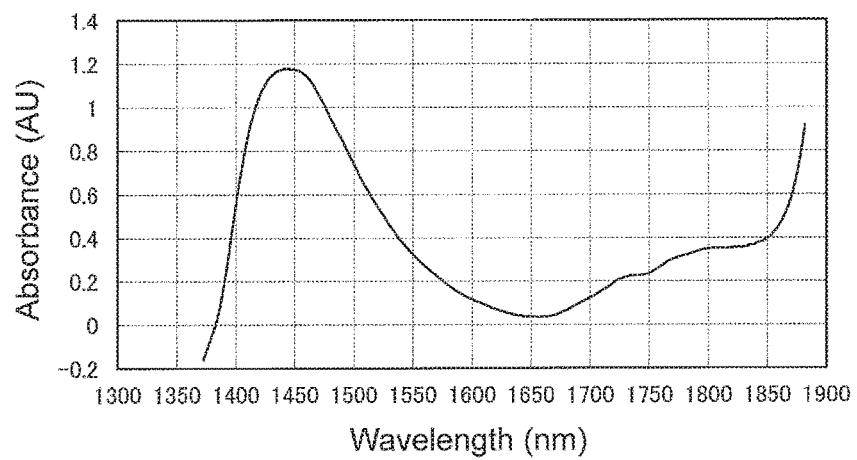
(b) 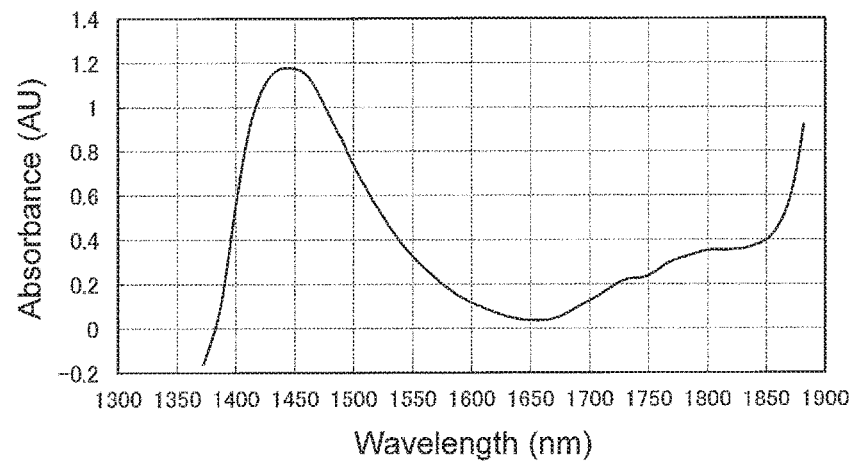
FIG. 4

$$\begin{bmatrix} W_{1450} & G_{1450} & F_{1450} \\ W_{1600} & G_{1600} & F_{1600} \\ W_{1727} & G_{1727} & F_{1727} \end{bmatrix} \begin{bmatrix} C_W \\ C_G \\ C_F \end{bmatrix} = \begin{bmatrix} \Delta OD_{1450} \\ \Delta OD_{1600} \\ \Delta OD_{1727} \end{bmatrix}$$

$$\begin{bmatrix} C_W \\ C_G \\ C_F \end{bmatrix} = \begin{bmatrix} W_{1450} & G_{1450} & F_{1450} \\ W_{1600} & G_{1600} & F_{1600} \\ W_{1727} & G_{1727} & F_{1727} \end{bmatrix}^{-1} \begin{bmatrix} \Delta OD_{1450} \\ \Delta OD_{1600} \\ \Delta OD_{1727} \end{bmatrix}$$

(a)

$$\begin{pmatrix} W_{1450} & G_{1450} & II_{1450}(\Delta s, \Delta f) \\ W_{1600} & G_{1600} & II_{1600}(\Delta s, \Delta f) \\ W_{1727} & G_{1727} & II_{1727}(\Delta s, \Delta f) \end{pmatrix} \begin{pmatrix} C_W \\ C_g \\ C_{II} \end{pmatrix} = \begin{pmatrix} \Delta OD_{1450} \\ \Delta OD_{1600} \\ \Delta OD_{1727} \end{pmatrix}$$

$$\begin{pmatrix} C_W \\ C_g \\ C_{II} \end{pmatrix} = \begin{pmatrix} W_{1450} & G_{1450} & II_{1450}(\Delta s, \Delta f) \\ W_{1600} & G_{1600} & II_{1600}(\Delta s, \Delta f) \\ W_{1727} & G_{1727} & II_{1727}(\Delta s, \Delta f) \end{pmatrix}^{-1} \begin{pmatrix} \Delta OD_{1450} \\ \Delta OD_{1600} \\ \Delta OD_{1727} \end{pmatrix}$$

Here, Δs=Δg+Δb: sum of change in glucose and change in baseline (b)

$$\begin{pmatrix} W_{1450} & G_{1450} & I2_{1450}(\Delta s, \Delta f) \\ W_{1600} & G_{1600} & I2_{1600}(\Delta s, \Delta f) \\ W_{1727} & G_{1727} & I2_{1727}(\Delta s, \Delta f) \end{pmatrix} \begin{pmatrix} C_W \\ C_{Error} \\ C_{I2} \end{pmatrix} = \begin{pmatrix} \Delta OD_{1450} \\ \Delta OD_{1600} \\ \Delta OD_{1727} \end{pmatrix}$$

$$\begin{pmatrix} C_W \\ C_{Error} \\ C_{I2} \end{pmatrix} = \begin{pmatrix} W_{1450} & G_{1450} & I2_{1450}(\Delta s, \Delta f) \\ W_{1600} & G_{1600} & I2_{1600}(\Delta s, \Delta f) \\ W_{1727} & G_{1727} & I2_{1727}(\Delta s, \Delta f) \end{pmatrix}^{-1} \begin{pmatrix} \Delta OD_{1450} \\ \Delta OD_{1600} \\ \Delta OD_{1727} \end{pmatrix}$$

Here, Δs=Δg+Δb: sum of change in glucose and change in baseline

FIG. 26

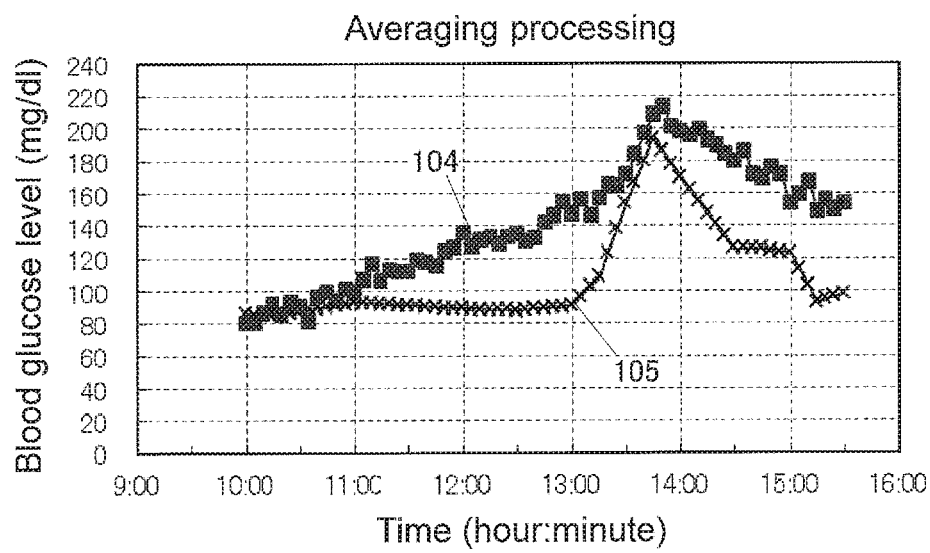
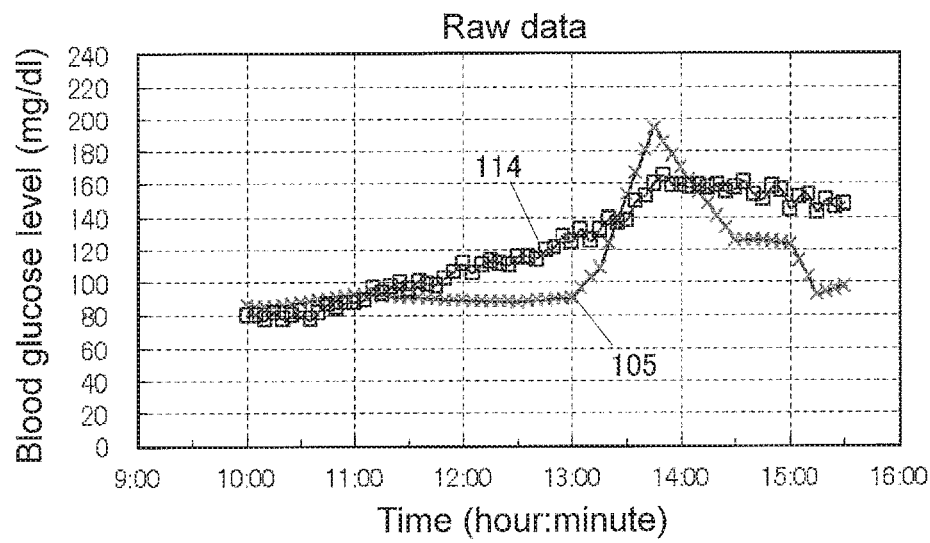
FIG. 27

FIG. 31

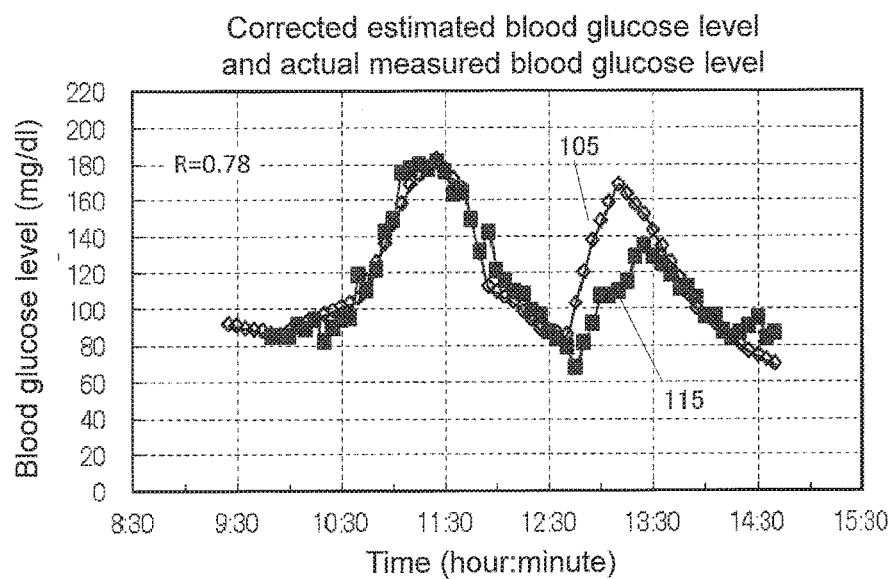

FIG. 32

$$\begin{pmatrix} W_{1450} & P_{1450} & G_{1450} & H_{1450}(\Delta s, \Delta f) \\ W_{1510} & P_{1510} & G_{1510} & H_{1510}(\Delta s, \Delta f) \\ W_{1600} & P_{1600} & G_{1600} & H_{1600}(\Delta s, \Delta f) \\ W_{1727} & P_{1727} & G_{1727} & H_{1727}(\Delta s, \Delta f) \end{pmatrix} \begin{pmatrix} C_W \\ C_P \\ C_G \\ C_H \end{pmatrix} = \begin{pmatrix} \Delta OD_{1450} \\ \Delta OD_{1510} \\ \Delta OD_{1600} \\ \Delta OD_{1727} \end{pmatrix}$$

$$\begin{pmatrix} C_W \\ C_P \\ C_G \\ C_H \end{pmatrix} = \begin{pmatrix} W_{1450} & P_{1450} & G_{1450} & H_{1450}(\Delta s, \Delta f) \\ W_{1510} & P_{1510} & G_{1510} & H_{1510}(\Delta s, \Delta f) \\ W_{1600} & P_{1600} & G_{1600} & H_{1600}(\Delta s, \Delta f) \\ W_{1727} & P_{1727} & G_{1727} & H_{1727}(\Delta s, \Delta f) \end{pmatrix}^{-1} \begin{pmatrix} \Delta OD_{1450} \\ \Delta OD_{1510} \\ \Delta OD_{1600} \\ \Delta OD_{1727} \end{pmatrix}$$

Here, $\Delta s = \Delta g + \Delta b$: sum of change in glucose and change in baseline $$\begin{bmatrix} W_{1450} & P_{1450} & G_{1450} & I2_{1450}(\Delta s, \Delta f) \\ W_{1510} & P_{1510} & G_{1510} & I2_{1510}(\Delta s, \Delta f) \\ W_{1600} & P_{1600} & G_{1600} & I2_{1600}(\Delta s, \Delta f) \\ W_{1727} & P_{1727} & G_{1727} & I2_{1727}(\Delta s, \Delta f) \end{bmatrix} \begin{bmatrix} C_W \\ C_P \\ C_{Error} \\ C_{I2} \end{bmatrix} = \begin{bmatrix} \Delta OD_{1450} \\ \Delta OD_{1510} \\ \Delta OD_{1600} \\ \Delta OD_{1727} \end{bmatrix}$$

$$\begin{bmatrix} C_W \\ C_P \\ C_{Error} \\ C_{I2} \end{bmatrix} = \begin{bmatrix} W_{1450} & P_{1450} & G_{1450} & I2_{1450}(\Delta s, \Delta f) \\ W_{1510} & P_{1510} & G_{1510} & I2_{1510}(\Delta s, \Delta f) \\ W_{1600} & P_{1600} & G_{1600} & I2_{1600}(\Delta s, \Delta f) \\ W_{1727} & P_{1727} & G_{1727} & I2_{1727}(\Delta s, \Delta f) \end{bmatrix}^{-1} \begin{bmatrix} \Delta OD_{1450} \\ \Delta OD_{1510} \\ \Delta OD_{1600} \\ \Delta OD_{1727} \end{bmatrix}$$

• Here, $\Delta s = \Delta g + \Delta b$: sum of change in glucose and change in baseline

FIG. 33

METHOD FOR QUANTIFYING GLUCOSE CONCENTRATION AND GLUCOSE CONCENTRATION MEASUREMENT DEVICE

PRIORITY

This is a National Stage Application under 35 U.S.C. § 365 of International Application PCT/JP2015/075189, with an international filing date of Sep. 4, 2015, which claims priority to Japanese Patent Application No. 2014-181283 filed on Sep. 5, 2014. The entire disclosures of International Application PCT/JP2015/075189 and Japanese Patent Application No. 2014-181283 are hereby incorporated herein by reference.

TECHNICAL FIELD

Certain implementations of the present invention relate to a method for quantifying a glucose concentration with which a glucose concentration in an intercellular fluid as an alternative characteristic of a blood glucose level of a living organism is quantified using diffusely reflected light or transmitted light of near-infrared light emitted onto a biological tissue, and a device for quantifying a glucose concentration.

BACKGROUND

For the purpose of quantitative analysis in near-infrared spectroscopy, multivariate methods such as principal component regression analysis and PLS regression analysis are frequently used. These methods are for performing multivariate analyses of spectral data obtained through experiments and the like, and a target component is quantified using a calibration curve (calibration model) obtained from experimental data.

In particular, for the purpose of a quantitative and qualitative analysis in a mid-infrared region, a method called a curve fitting method with which a composite spectrum including a large number of peaks resulting from light absorption characteristics of a plurality of components is divided into component spectra of the components is known as another conventional method.

The curve fitting method is frequently used in the case where the absorption peaks of the components at specific absorption wavelengths are sharp and clear as in a mid-infrared spectrum. However, in the case of the near-infrared spectrum, there have been few examples in which the curve fitting method is used other than the method for measuring a hemoglobin concentration and there are no precedents in which the curve fitting method has been used to quantify a glucose concentration.

Also, a method called CLS (classical least squares) is known as a similar conventional method with which a spectrum is synthesized using component spectra.

The CLS method is also frequently used in a spectroscopic analysis in a mid-infrared region and is for synthesizing a measurement spectrum using component spectra as parameters. The CLS method is a method to which the Lambert-Beer law, which states that absorbance is in proportion to a concentration and a length of a light path, is applied to a multi-component (multi-factor) component analysis as it is. There are also no precedents in which this method has been used to quantify a glucose concentration.

The following are the advantages of the CLS method:
It is important to estimate the number of components to be used in synthesis of a spectrum, and when the estimation is accurate, accurate quantification can be performed.
Since the spectra of biological components are used, the meanings of parameters are clear.
In contrast, the following are said to be the drawbacks:
If the estimation of unexpected disturbance factors, particularly the number of components, has been misread, the quantification accuracy will decrease.
The above-mentioned number of components includes the number of unpredictable components, device errors, and the like.

The reason why the above-mentioned two conventional methods are not frequently used in the near-infrared spectroscopy is that in the near-infrared spectrum, the component spectra have a broad shape and do not include clear absorption peaks, and that when a minor component such as a glucose component in a living organism is analyzed, a spectral change in the minor component is smaller than spectral changes in other components, and thus it is difficult to apply the spectrum synthesis methods such as the curve fitting method and the CLS method.

SUMMARY

As described above, in the near-infrared spectrum, the component spectra have a broad shape and do not include clear absorption peaks, and when a minor component such as a glucose component in a living organism is analyzed, a spectral change in the minor component is smaller than spectral changes in other components.

Therefore, it is difficult to apply the spectrum synthesis methods such as the curve fitting method and the CLS method in the conventional manner to the quantification of the minor component using a near-infrared spectrum, and to perform quantification with high reproducibility using a calibration curve (calibration model) produced by performing a multivariate analysis of actual data.

Also, another reason why it is difficult to apply the above-mentioned methods is that the shape of a change in the spectrum of a glucose component is similar to the shape of a change in the spectrum of the baseline, and thus it is difficult to separate the two spectra. This is also a factor in impairing reproducibility and increasing errors measurement.

An object of certain implementations of the present invention is to provide a method for quantifying a glucose concentration that enables realization of a measurement algorithm having disturbance-mixing resistance, high reproducibility, and high accuracy, and a glucose concentration measurement device.

In order to solve the foregoing problems, a method for quantifying a glucose concentration according to a first aspect of the present invention is a method for quantifying a glucose concentration in which near-infrared light is emitted onto a living organism and a glucose concentration in a biological tissue is measured using a signal obtained by receiving diffusely reflected light or transmitted light from the biological tissue, and includes a concentration index calculation step and a glucose concentration calculation step. In the concentration index calculation step, a concentration index of a glucose component is calculated by using at least a spectrum of a water component, a spectrum of a glucose component, and a spectrum of a fat component to synthesize a difference spectrum between a measurement spectrum at a time of measurement of a glucose concentration and a spectrum serving as a reference obtained prior to the measurement spectrum. In the glucose concentration calculation step, a glucose concentration in the living organism is calculated using the calculated concentration index.

A method for quantifying a glucose concentration according to a second aspect of the present invention is the method for quantifying a glucose concentration according to the first aspect of the present invention, wherein, in the concentration index calculation step, the concentration index of the glucose component is calculated by using at least three absorption signals that are an absorption signal at a first characteristic wavelength selected from 1450±30 nm, which is a characteristic wavelength range of the water component, as an index indicating the spectrum of the water component, an absorption signal at a second characteristic wavelength selected from 1600±30 nm, which is a characteristic wavelength range of the glucose component, as an index indicating the spectrum of the glucose component, and an absorption signal at a third characteristic wavelength selected from 1727±30 nm, which is a characteristic wavelength range of the fat component, as an index indicating the spectrum of the fat component.

A method for quantifying a glucose concentration according to a third aspect of the present invention is the method for quantifying a glucose concentration according to the second aspect of the present invention, wherein, in the concentration index calculation step, a square matrix is produced using absorption signals of the spectrum of the water component, the spectrum of the glucose component, and the spectrum of the fat component at the first characteristic wavelength, absorption signals of the spectrum of the water component, the spectrum of the glucose component, and the spectrum of the fat component at the second characteristic wavelength, and absorption signals of the spectrum of the water component, the spectrum of the glucose component, and the spectrum of the fat component at the third characteristic wavelength, and the concentration index of the glucose component is calculated using an inverse matrix of the square matrix.

A method for quantifying a glucose concentration according to a fourth aspect of the present invention is the method for quantifying a glucose concentration according to the first aspect of the present invention, and further includes a first imaginary spectrum producing step. In the first imaginary spectrum producing step, a first imaginary spectrum is produced based on, in the measurement spectrum at the time of the measurement of a glucose concentration, a characteristic wavelength of a baseline variation and a characteristic wavelength of the spectrum of the fat component. In the concentration index calculation step, the concentration index of the glucose component is calculated using the first imaginary spectrum instead of the spectrum of the fat component.

A method for quantifying a glucose concentration according to a fifth aspect of the present invention is the method for quantifying a glucose concentration according to the fourth aspect of the present invention, wherein, in the first imaginary spectrum producing step, the first imaginary spectrum and the second imaginary spectrum are produced based on absorbances at characteristic wavelengths selected from a wavelength range of 1727±30 nm, which are the characteristic absorption wavelengths of the spectrum of the fat component, and a characteristic wavelength range of 1650±30 nm of a spectral variation caused by the baseline variation.

A method for quantifying a glucose concentration according to a sixth aspect of the present invention is the method for quantifying a glucose concentration according to the fourth or fifth aspect of the present invention, wherein, in the first imaginary spectrum producing step, the first imaginary spectrum is produced based on, in the measurement spectrum at the time of the measurement of a glucose concentration, a characteristic wavelength of the baseline variation and a characteristic wavelength of the spectrum of the fat component, which have undergone smoothing processing.

A method for quantifying a glucose concentration according to a seventh aspect of the present invention is the method for quantifying a glucose concentration according to the fourth aspect of the present invention, wherein the measurement spectrum or difference spectrum, the spectrum of the water component, the spectrum of the glucose component, and the first imaginary spectrum are normalized at a wavelength selected from 1400±20 nm.

A method for quantifying a glucose concentration according to an eighth aspect of the present invention is the method for quantifying a glucose concentration according to the sixth aspect of the present invention, and further includes a second imaginary spectrum producing step, an error concentration index calculation step, and a correcting step. In the second imaginary spectrum producing step, a second imaginary spectrum is produced based on, in the measurement spectrum, the characteristic wavelength of the baseline variation and the characteristic wavelength of the spectrum of the fat component, which have not undergone the smoothing processing. In the error concentration index calculation step, an error concentration index is calculated by using at least the spectrum of the water component, the spectrum of the glucose component, and the second imaginary spectrum to synthesize the difference spectrum. In the correcting step of correcting the calculated concentration index using the calculated error concentration index. In the glucose concentration calculation step, a glucose concentration in a living organism is calculated using the corrected concentration index.

A method for quantifying a glucose concentration according to a ninth aspect of the present invention is the method for quantifying a glucose concentration according to the eighth aspect of the present invention, wherein, in the second imaginary spectrum producing step, the first imaginary spectrum and the second imaginary spectrum are produced based on absorbances at characteristic wavelengths selected from a wavelength range of 1727±30 nm, which are the characteristic absorption wavelengths of the spectrum of the fat component, and a characteristic wavelength range of 1650±30 nm of a spectral variation caused by the baseline variation.

A method for quantifying a glucose concentration according to a tenth aspect of the present invention is the method for quantifying a glucose concentration according to the eighth or ninth aspect of the present invention, wherein the measurement spectrum or difference spectrum, the spectrum of the water component, the spectrum of the glucose component, the first imaginary spectrum, and the second imaginary spectrum are normalized at a wavelength selected from 1400±20 nm.

A method for quantifying a glucose concentration according to an eleventh aspect of the present invention is the method for quantifying a glucose concentration according to any of the eighth to tenth aspects of the present invention, wherein, in the correcting step, the correction using the error concentration index is performed by subtracting the calculated error concentration index from the calculated concentration index of the glucose component.

A method for quantifying a glucose concentration according to a twelfth aspect of the present invention is the method for quantifying a glucose concentration according to the eighth aspect of the present invention, wherein, in the concentration index calculation step, a concentration index of a glucose component is calculated by using the spectrum of the water component, the spectrum of the glucose component, the first imaginary spectrum, and a spectrum of a protein component to synthesize a difference spectrum between the measurement spectrum and a spectrum serving as a reference obtained prior to the measurement spectrum. In the error concentration index calculation step, an error concentration index is calculated by using at least the spectrum of the water component, the spectrum of the glucose component, the second imaginary spectrum, and the spectrum of the protein component to synthesize the difference spectrum.

A glucose concentration measurement device according to a thirteenth aspect of the present invention includes a light source, a light receiving unit, a concentration index calculation unit, and a glucose concentration calculation unit. The light source emits near-infrared light. The light receiving unit receives light that has been emitted onto a surface of a living organism by the light source and that is transmitted or reflected by the living organism and then subjected to spectroscopy. The concentration index calculation unit calculates a concentration index of a glucose component by using at least a spectrum of a water component, a spectrum of a glucose component, and a spectrum of a fat component to synthesize a difference spectrum between a measurement spectrum at a time of measurement of a glucose concentration and a spectrum serving as a reference obtained prior to the measurement spectrum. A glucose concentration calculation unit calculates a glucose concentration in the living organism using the calculated concentration index.

A glucose concentration measurement device according to a fourteenth aspect of the present invention is the glucose concentration measurement device according to the thirteenth aspect of the present invention, and further includes a first imaginary spectrum producing unit. The first imaginary spectrum producing unit produces a first imaginary spectrum based on, in a measurement spectrum at the time of measurement of a glucose concentration, a characteristic wavelength of a baseline variation and a characteristic wavelength of the spectrum of the fat component, which have undergone smoothing processing. The concentration index calculation unit calculates the concentration index of the glucose component using the first imaginary spectrum instead of the spectrum of the fat component.

A glucose concentration measurement device according to a fifteenth aspect of the present invention is the glucose concentration measurement device according to the fourteenth aspect of the present invention, and further includes a second imaginary spectrum producing unit, an error concentration index calculation unit, and a correcting unit. The second imaginary spectrum producing unit produces a second imaginary spectrum based on, in the measurement spectrum, the characteristic wavelength of the baseline variation and the characteristic wavelength of the spectrum of the fat component, which have not undergone the smoothing processing. The error concentration index calculation unit calculates an error concentration index by using at least the spectrum of the water component, the spectrum of the glucose component, and the second imaginary spectrum to synthesize the difference spectrum. The correcting unit corrects the calculated concentration index using the calculated error concentration index. The glucose concentration calculation unit calculates a glucose concentration in a living organism using the corrected concentration index.

With the certain implementations of present invention, it is possible to provide a method for quantifying a glucose concentration that enables realization of a measurement algorithm having disturbance-mixing resistance, high reproducibility, and high accuracy, and a glucose concentration measurement device.

BRIEF DESCRIPTION OF THE DRAWINGS

FIG. 1 is a schematic view of a glucose concentration measurement device of an implementation of the present invention.

FIG. 4(a) is a reference spectrum measured with the method for quantifying a glucose concentration shown in FIG. 3, and FIG. 4(b) is a measurement spectrum measured with the method for quantifying a glucose concentration shown in FIG. 3.

FIGS. 26(a) and 26(b) are explanatory diagrams of a determinant used for the synthesis of a spectrum in an implementation of the present invention.

FIGS. 27(a) and 27(b) are diagrams for comparing an estimated blood glucose level obtained by performing smoothing processing and an estimation error obtained without performing smoothing processing.

FIG. 31 is an explanatory diagram of an actual measured blood glucose level and an estimated blood glucose level.

FIG. 32 is an explanatory diagram of a determinant used for the synthesis of a spectrum in an implementation of the present invention.

FIG. 33 is an explanatory diagram of a determinant used for the synthesis of a spectrum in an implementation of the present invention.

DETAILED DESCRIPTION

Figure 2:
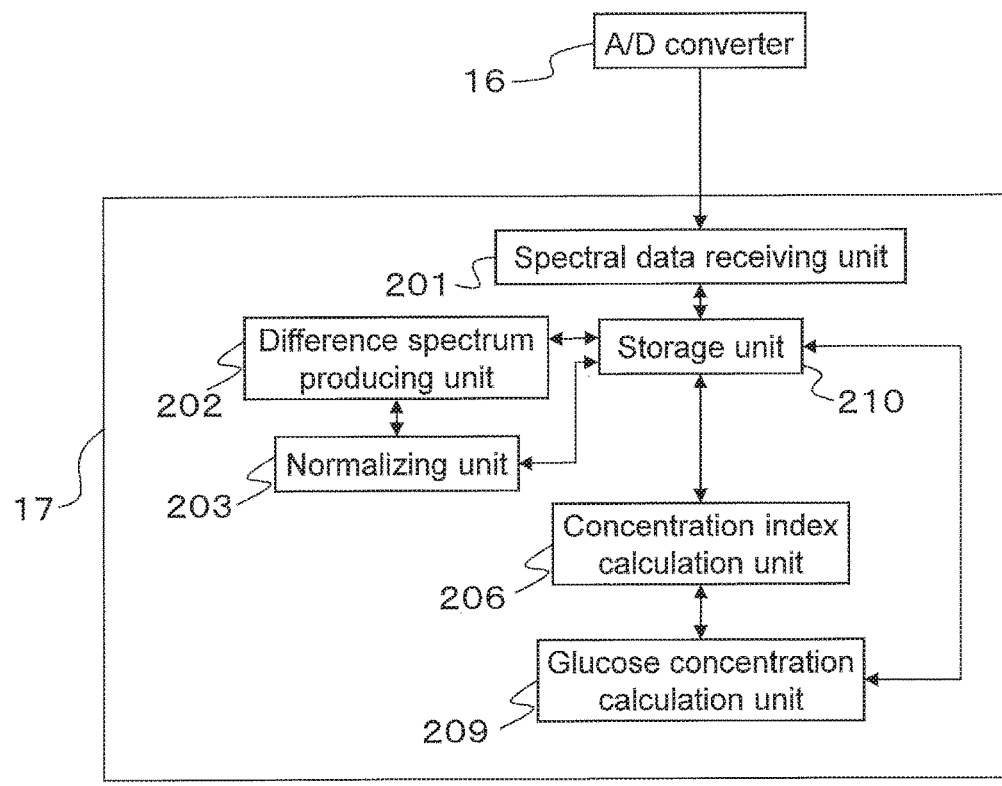
FIG. 2 is a block diagram illustrating a configuration of an arithmetic device of a glucose concentration measurement device of Embodiment 1.

Hereinafter, embodiments according to the present invention will be described with reference to the drawings.

Embodiment 1

A glucose concentration measurement device and a method for measuring a glucose concentration of Embodiment 1 according to the present invention will be described. It should be noted that this description describes the glucose contained in blood and the glucose contained in the intercellular fluid using different terms: "blood glucose" and "glucose", respectively. In particular, when a blood glucose level is estimated, the estimated glucose concentration is used as the blood glucose level.

1-1. Glucose Concentration Measurement Device

A glucose concentration measurement device according to this embodiment will be described with reference to FIG. 1. First, near-infrared light emitted from a halogen lamp 1 is incident on a biological tissue 6 (in the Embodiment 1, skin of a person to be subjected to blood glucose measurement) via a heat shielding plate 2, a pinhole 3, a lens 4, an optical fiber bundle 5A, and a measurement probe 9. One end of a measurement optical fiber 7 and one end of a reference optical fiber 8 are connected to the optical fiber bundle 5A. The other end of the measurement optical fiber 7 is connected to the measurement probe 9, and the other end of the reference optical fiber 8 is connected to a reference probe 10. In addition, the measurement probe 9 is connected to a measurement-side emitting body 11 via an optical fiber 5B, and the reference probe 10 is connected to a reference-side emitting body 12 via the optical fiber 5B.

When a near-infrared spectrum is measured by bringing a tip surface of the measurement probe 9, serving as a sensing means, into contact with the surface of the biological tissue 6, near-infrared light that is incident from the halogen lamp 1, serving as a light source, into the optical fiber bundle 5A is transmitted through the measurement optical fiber 7, and is emitted on the surface of the biological tissue 6 from twelve light-emitting fibers 20 that are arranged on the circumference of a concentric circle at the tip of the measurement probe 9 as shown in FIG. 1(b). This measurement light emitted on the biological tissue 6 is diffusely reflected in the biological tissue 6, and then a portion of the diffusely reflected light is received by a light receiving-side optical fiber 19 that is arranged at the tip of the measurement probe 9. The received light is emitted from the measurement-side emitting body 11 via this light receiving-side optical fiber 19. The light emitted from the measurement-side emitting body 11 is incident into a diffraction grating 14 through a lens 13, is subjected to spectroscopy, and is then detected by a light-receiving element 15.

Light signals detected by the light-receiving element 15 undergo AD conversion by an A/D converter 16 and then are inputted into an arithmetic device 17 such as a personal computer.

Reference measurement is performed by measuring light reflected from a reference plate 18 made of ceramic or the like, and this reflected light is used as reference light.

That is, near-infrared light that is incident from the halogen lamp 1 into the optical fiber bundle 5A passes through the reference optical fiber 8, and is emitted onto the surface of the reference plate 18 from the tip of the reference probe 10. Light that is emitted onto the reference plate 18 and then reflected therefrom is emitted from the reference-side emitting body 12 via the light receiving-side optical fiber 19 arranged at the tip of the reference probe 10.

Shutters 21 are arranged between the measurement-side emitting body 11 and the lens 13 mentioned above and between the reference-side emitting body 12 and a lens 13, and either of the light from the measurement-side emitting body 11 and the light from the reference-side emitting body 12 selectively passes through with opening/closing of the shutters 21.

Both the end surface of the measurement probe 9 and the end surface of the reference probe 10 include the twelve light-emitting fibers 20 arranged in a circle and one light receiving-side optical fiber 19 arranged at the center of the circle as shown in FIG. 1(b). A distance L between the center of the light-emitting fiber 20 and the center of the light receiving-side optical fiber 19 is set to be 0.3 mm or more and 2 mm or less, and preferably 0.65 mm.

Control Configuration of Arithmetic Device

FIG. 2 is a block diagram illustrating a control configuration of the arithmetic device 17 of the glucose concentration measurement device of this Embodiment 1.

As shown in FIG. 2, the arithmetic device 17 of the glucose concentration measurement device of this embodiment includes a spectral data receiving unit 201, a difference spectrum producing unit 202, a normalizing unit 203, a concentration index calculation unit 206, a glucose concentration calculation unit 209, and a storage unit 210.

The spectral data receiving unit 201 receives spectral data that has undergone digital conversion by the A/D converter 16 and sends the data to the storage unit 210.

The difference spectrum producing unit 202 computes the difference between a spectrum that is received by the spectral data receiving unit 201 at the time of the measurement of a glucose concentration and a reference spectrum that is received therebefore and stored in the storage unit 210, and produces a difference spectrum.

The normalizing unit 203 normalizes the difference spectrum by subtracting an absorbance of the difference spectrum at 1400 nm from the absorbances of the difference spectrum.

The concentration index calculation unit 206 uses spectral data of a water component, spectral data of a glucose component, and spectral data of a fat component that are stored in the storage unit 210 to synthesize the difference spectrum determined by subtracting the reference spectrum from the spectrum obtained at the time of the measurement of a glucose concentration and normalizing the resulting spectrum, and calculates a concentration index CG.

The glucose concentration calculation unit 209 calculates a glucose concentration by multiplying the concentration index CG, which was calculated by the concentration index calculation unit 206, by a conversion factor stored in the storage unit 210.

The conversion factor to be used to convert a concentration index CG value into a change in the glucose concentration, the spectral data at the time of the measurement of a glucose concentration, the reference spectral data, the difference spectrum, the difference spectrum normalized at 1400 nm, the spectral data of a water component, the spectral data of a glucose component, the spectral data of a fat component, and the like are stored in the storage unit 210.

1-2. Method for Measuring Blood Glucose Level

Hereinafter, a method for measuring a blood glucose level (an example of a method for quantifying a glucose concentration) will be described.

A procedure to measure a blood glucose level of a person to be subjected to blood glucose measurement using the above-described glucose concentration measurement device will be described.

Figure 3:
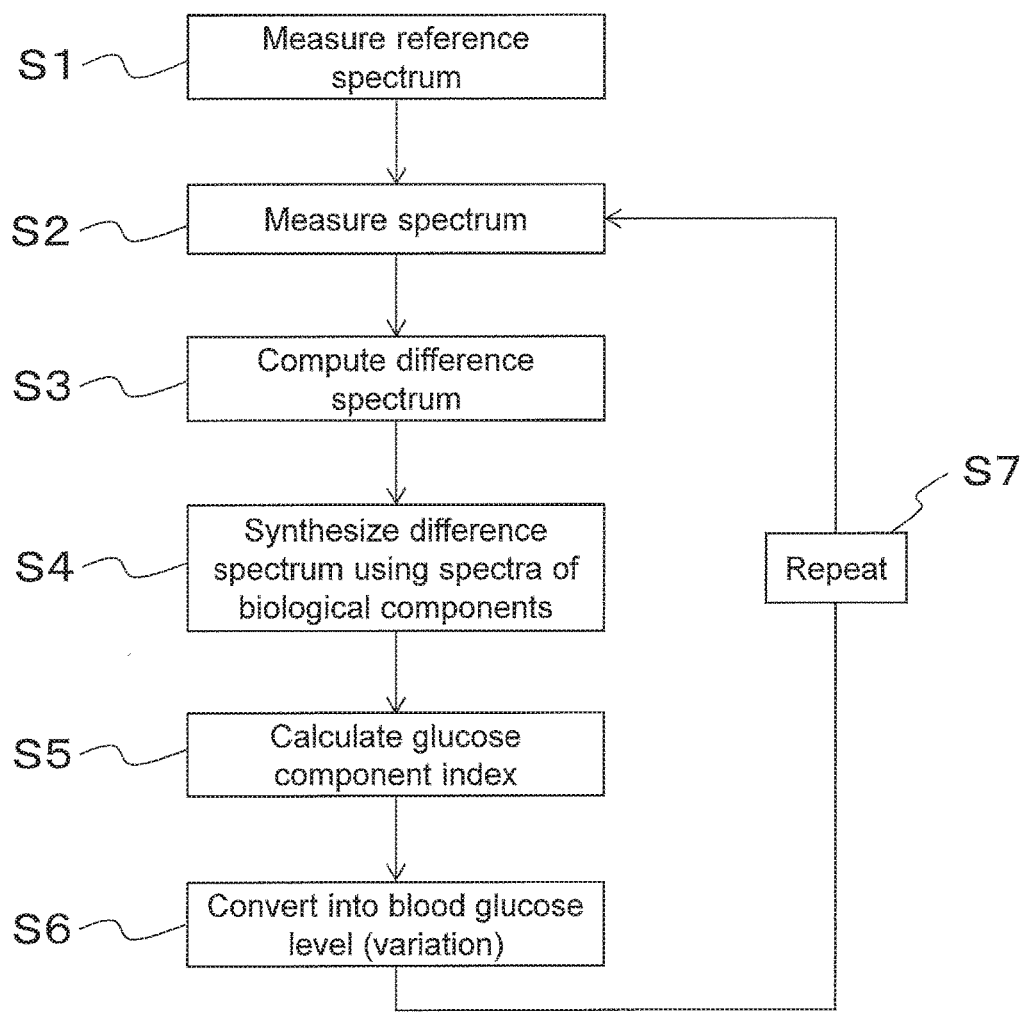
FIG. 3 is a flowchart illustrating a measurement procedure in a method for quantifying a glucose concentration of the Embodiment 1.

FIG. 3 is a flowchart illustrating a method for measuring a blood glucose level of this Embodiment 1.

(1) First, the above-described measurement probe 9 shown in FIG. 1(b) is attached to the inner side of the left forearm of a person to be subjected to blood glucose level measurement, using a double-sided adhesive tape to the extent of slight contact with a contact pressure of 10 g-weight/cm$^2$, for example.

(2) After a lapse of about 30 minutes since the measurement probe 9 is attached, spectral measurement of skin tissue is started. At the same time, a blood glucose level of collected blood is measured using a blood glucose level measurement device that has been separately prepared, and the results are inputted into the arithmetic device 17 and used as an initial value (V0) of the blood glucose level. A spectrum measured at the start of the spectral measurement is set to be a reference spectrum (step S1). FIG. 4(a) is a diagram showing a reference spectrum. The arithmetic device 17 receives the reference spectrum via the spectral data receiving unit 201 and stores the reference spectrum in the storage unit 210.

(3) The blood glucose level is predicted according to the following procedure using the spectra measured for the skin tissue every 5 minutes.

1) Spectral measurement is performed in order to measure a blood glucose level, and a measurement spectrum is obtained (step S2). The arithmetic device 17 receives the measurement spectrum via the spectral data receiving unit 201 and stores the measurement spectrum in the storage unit 210.

Figure 5:
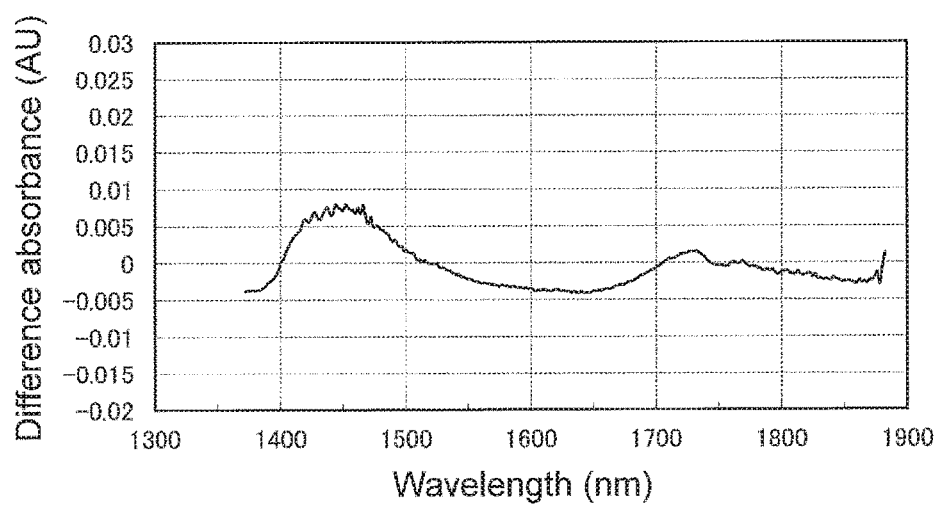
FIG. 5 is a difference spectrum (difference spectrum between the reference spectrum shown in FIG. 4(a) and the measurement spectrum shown in FIG. 4(b)) normalized at 1400 nm.

2) The difference spectrum producing unit 202 determines the difference between the measurement spectrum and the reference spectrum and calculates the difference spectrum (see step S3). FIG. 4(b) shows, as an example, a diffuse reflectance spectrum obtained after a lapse of 2 hours from when the reference spectrum was measured. The difference between this diffuse reflectance spectrum after 2 hours and the reference spectrum is calculated, and thus the difference spectrum shown in FIG. 5 is obtained. It should be noted that the difference spectrum shown in FIG. 5 is obtained by the normalizing unit 203 normalizing the difference spectrum between the measurement spectrum and the reference spectrum, based on the absorbance at 1400 nm. "Normalization" means that the absorbance at 1400 nm is subtracted from the absorbances (examples of an absorption signal) at respective wavelengths. Therefore, as shown in FIG. 5, the absorbance at 1400 nm is 0. The normalization is performed for the purpose of reducing disturbance generated due to various factors during the measurement.

3) The concentration index calculation unit 206 synthesizes a difference spectrum using at least a spectrum of a water component, a spectrum of a glucose component, and an imaginary spectrum (step S4), and thus the concentration index CG of the glucose component is calculated (step S5). A determinant of a square matrix based on the absorbances at the characteristic wavelengths of the components is used in the synthesis.

Figures 6, 7:
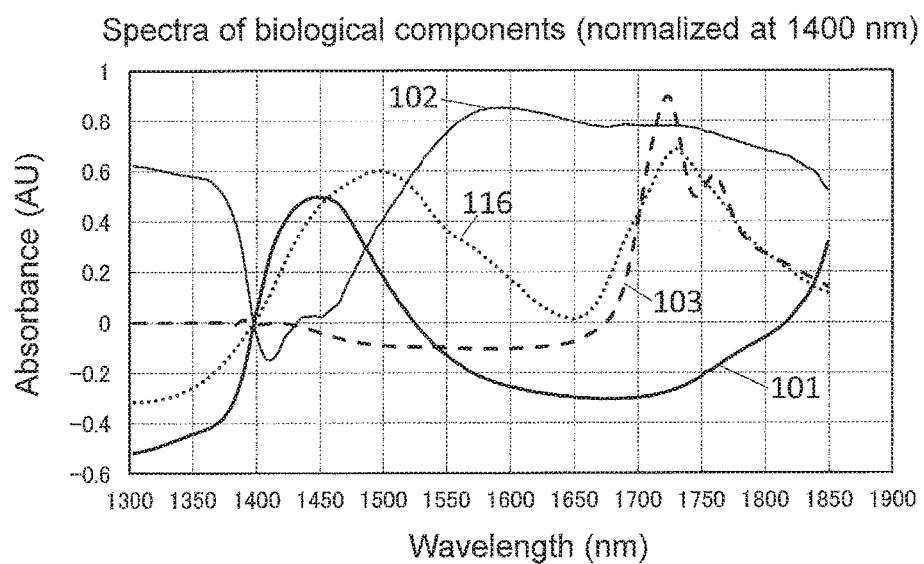
FIG. 6 is an explanatory diagram of spectra of biological components normalized at 1400 nm that are to be used to synthesize the difference spectrum.
FIG. 7 is an explanatory diagram of a determinant used to synthesize a difference spectrum in an implementation of the present invention.

The synthesis of a spectrum is performed according to the following procedure. Step S4 and step S5 correspond to an example of a concentration index calculation step.

a) A square matrix with three rows and three columns is produced based on the absorbances at 1450 nm, which is a specific absorption wavelength of water 101, the absorbances at 1600 nm, which is a specific absorption wavelength of a glucose component 102, and the absorbances at 1727 nm, which is a specific absorption wavelength of a fat component 103, in the respective spectra of the biological components shown in FIG. 6.

The spectra of the biological components shown in FIG. 6 are normalized based on the absorbances at 1400 nm. FIG. 7 is a diagram illustrating a determinant (three rows and three columns) to be used to synthesize a difference spectrum. As shown in FIG. 7, difference absorbances at the respective wavelengths are obtained by multiplying the square matrix, which was produced based on the absorbances of the spectra of the biological components at the respective wavelengths, by concentration indices (changes from the concentration index at the time of the measurement of the reference spectrum) of the respective components. In this formula, W represents a water component, G represents a glucose component, F represents a fat component, C represents a component concentration index, ΔOD represents a difference absorbance, and a subscript on the right side represents a corresponding wavelength or a component. For example, W1450 represents an absorbance of a water component at 1450 nm, and CW represents a concentration index of a water component.

b) Difference absorbances at the respective wavelengths are obtained by multiplying the square matrix, which was produced based on the absorbances of the spectra of the biological components at the respective wavelengths, by concentration indices (changes from the concentration index at the time of the measurement of the reference spectrum) of the respective components.

c) A square matrix has an inverse matrix, and therefore, as shown in FIG. 7, when the right and left terms of the determinant are multiplied using the calculated inverse matrix in the same direction, the concentration indices of the respective components can be determined as the products of the inverse matrix and the difference spectra.

With this procedure, the concentration indices after a lapse of 2 hours from when the reference spectrum was measured can be obtained by synthesizing the difference spectrum shown in FIG. 5 between the measurement spectrum after a lapse of 2 hours and the reference spectrum using the spectrum of the water component 101, the spectrum of the glucose component 102, and the spectrum of the fat component 103 shown in FIG. 6.

4) The glucose concentration calculation unit 209 calculates a blood glucose level using the concentration index of the glucose component. A conversion factor ($\alpha$) that is determined in advance is used to calculate a glucose concentration using the glucose concentration index (step S6). Specifically, the amount of change in the glucose concentration is calculated by computing the product of the conversion factor ($\alpha$) and the concentration index (CG). A glucose concentration (Vt) at the time of measurement of a measurement spectrum is calculated by adding a blood glucose level (V0) measured using collected blood at the time of measurement of a reference spectrum to the amount of change in the blood glucose level. That is, the blood glucose level Vt is calculated according to an equation Vt=V0+$\alpha$×CG. This step S6 corresponds to an example of a glucose calculation step.

5) Since the spectral measurement of the skin tissue is performed every 5 minutes, the blood glucose level is continuously predicted every 5 minutes.

It should be noted that the conversion factor is determined in advance using a specific glucose measurement device for a specific patient. The conversion factor can be determined by using the blood glucose levels of collected blood and the glucose concentration indices for concentrations at a plurality of places to divide the blood glucose levels by the glucose concentration indices and determine an average, for example.

The changes in the blood glucose level obtained by measuring the blood glucose level every 5 minutes as described above is shown in FIG. 11 of Example 1, which will be described later, as an estimated blood glucose level 104.

As described above, with the glucose concentration measurement device of this embodiment, by merely measuring the conversion factor in advance and performing blood glucose level measurement using collected blood when a reference spectrum is measured, further measurement of glucose concentration can be noninvasively performed without collecting blood. Therefore, when a change over time in the glucose concentration in a patient is monitored, the load on the patient can be reduced as much as possible. The glucose concentration measurement device of this embodiment is useful in a case where it is necessary to monitor a change in the blood glucose level of a patient at all times in a hospital, for example.

The measurement may be performed automatically, and a patient may be able to check the measurement value as needed. For example, if a patient wears the glucose concentration measurement device of this embodiment in the morning, and measurement using collected blood is simultaneously performed at the time of the measurement of a reference spectrum, the changes in the blood glucose level over a day can be measured noninvasively. Based on these changes in the blood glucose level, guidance for improving lifestyle and the like can be provided.

Furthermore, in this embodiment, it is not necessary to perform the measurement at every predetermined time (5 minutes), and the measurement may be performed only when required. For example, a change in the glucose concentration between before and after a meal may be measured.

Next, the glucose concentration measurement device and the method for quantifying a glucose concentration according to this Embodiment 1 will be described in detail by way of Example 1, which is an experimental example.

1-3. Example 1

Example 1 is an experimental example in which the concentration index of the glucose component in the skin tissue is determined using a diffuse reflectance spectrum of the skin tissue, and the change in the blood glucose level is calculated.

In the calculation of a change in the index of the glucose concentration in the skin tissue, the measurement spectrum at the start of the experiment is used as a reference, and the difference from the measurement spectrum at the time when it is desired to determine a glucose concentration is determined first to calculate a difference spectrum. Then, this difference spectrum is synthesized using the respective spectra of the water component, glucose component, and fat component, which cause the change, and the change in the blood glucose level is calculated by determining a glucose concentration index that matches the difference spectrum.

A method for producing a determinant using the specific absorption wavelengths of water, glucose, and fat was used as a method for synthesizing a spectrum.

With this method, a component spectrum that has a broad shape and does not include a sharp absorption peak, as is such in a near-infrared spectrum, can be analyzed without being affected by disturbance. In addition, it is easy to perform the analysis, the computation can be performed in a short time, and thus a high-performance CPU and a large-capacity memory are not required. Accordingly, the reduction in size and cost of the measurement device is expected, and there is an advantage in that the method is useful for intuitive understanding of the phenomenon because the spectra of the biological components are used as parameters.

The experimental procedure and analysis method used in Example 1 will be described below. In this experiment, a glucose load was provided orally to a healthy subject, and the change in the blood glucose level was quantified.

In Example 1, the glucose concentration measurement device described in FIG. 1 was used.

The measurement probe 9 as shown in FIG. 1(b) having a configuration in which the twelve light-emitting fibers 20 were arranged on a circumference of a circle having a radius L of 0.65 mm around the light receiving-side optical fiber 19 having a diameter of 0.2 mm as a center was used to perform spectral measurement with near-infrared light using the above-mentioned measurement device on the subject in a sitting posture. This measurement probe 9 was attached to the inner side of the left forearm using a double-sided adhesive tape to the extent of slight contact with a contact pressure of 10 g-weight/cm$^2$, and the measurement of a near-infrared absorption spectrum in a wavelength range from 1350 nm to 1900 nm was repeated at 5-minute intervals.

It is possible to selectively measure signals from a dermiss tissue at a depth of about 0.5 mm from the surface of the skin by using the measurement probe 9 emitting and receiving light at the above-mentioned intervals and by measuring the skin tissue at the above-mentioned wavelength. Also, as reference data, the blood glucose level of collected blood was measured using a simple blood glucose monitor at 15-minute intervals in synchronization with timing at which the blood glucose level was measured with the near-infrared light. At two time points after a lapse of 5 minutes and a lapse of 10 minutes at which the measurement of a blood glucose level corresponding to the measurement of the spectrum in the skin tissue was not performed, the blood glucose levels were estimated by performing a linear interpolation based on the measurement results of blood glucose levels that were actually measured using collected blood prior to and subsequent to these time points.

A glucose load was provided orally after a lapse of about 45 minutes from which the measurement of the spectrum in the skin tissue was started and the blood glucose level of the subject was artificially varied. 200 ml of a liquid beverage (Calorie Mate in a can, manufactured by Otsuka Pharmaceutical Co., Ltd.) containing about 40 g of glucose was used as a glucose load. The spectral measurement and the measurement of the blood glucose level of collected blood were performed until the blood glucose level stabilized at a level not higher than 100 mg/dL, which is a normal value, that is, for about 3 to 4 hours, after the measurement was started.

Figure 8:
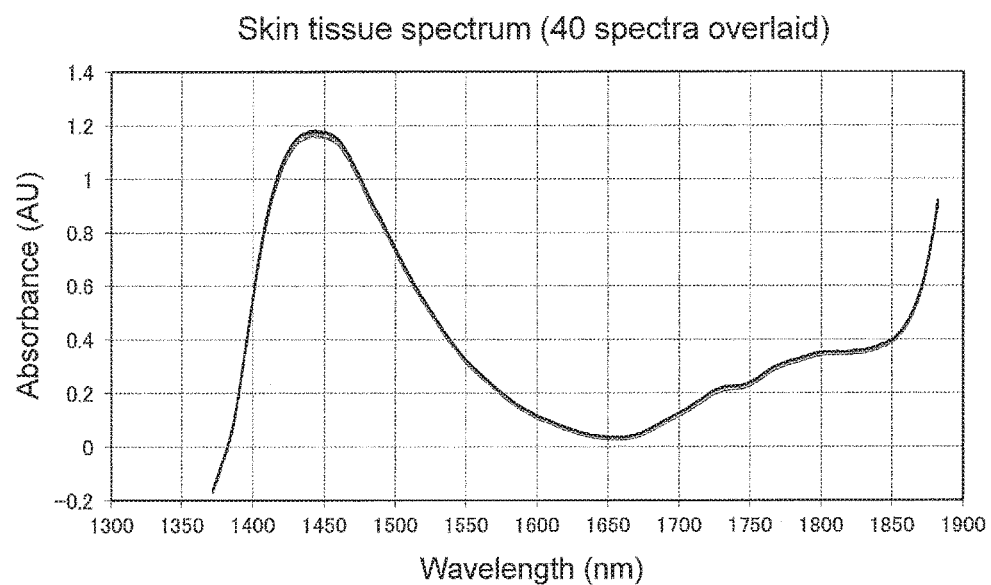
FIG. 8 is an explanatory diagram illustrating a diffuse reflectance spectrum in skin tissue.

FIG. 8 is a diagram illustrating an example of a near-infrared diffuse reflectance spectrum (wavelength range from 1350 to 1900 nm) measured for the skin tissue using the above-described glucose concentration device (FIG. 1). The spectrum measured for the skin tissue shown in the diagram was obtained by overlaying about 40 spectra measured every 5 minutes after starting the measurement. As shown in FIG. 8, the spectra measured at different time points at which the blood glucose levels were different were plotted together, but only a line in which the spectra were densely overlaid is confirmed, and it is not possible to visually identify the change over time in the spectrum during the measurement of the skin tissue and the changes due to the difference in the blood glucose level.

Therefore, in order to identify a spectral change over time, in this embodiment, the spectrum measured for the skin tissue at the start of the measurement was used as a reference spectrum, and a difference spectrum obtained by subtracting the reference spectrum from the spectrum measured thereafter was used.

In this embodiment, a spectrum measured at a time point after a lapse of a certain period of time at which the measurement spectrum stabilized (after a lapse of about 45 minutes from which the sensor was attached) was used as a reference spectrum, but a spectrum to be used as a reference spectrum is not limited thereto, and a reference spectrum as specified in the following (i) and (ii) may be used, for example.

(i) Standards for judging the stability of the measurement spectrum are provided, and a measurement spectrum at that time point is used as a reference spectrum.

(ii) A spectrum obtained by averaging some or all of the spectra is used as a reference spectrum.

Furthermore, in the embodiment of this application, the difference spectra obtained by determining the differences from the reference spectrum are normalized based on the absorbances at 1400 nm, for the purpose of reducing disturbance due to various factors during the measurement. In the actual calculations, the absorbance at 1400 nm is subtracted from absorbances at other wavelengths in each measurement spectrum. Therefore, the absorbance at 1400 nm is 0 in each difference spectrum.

Figure 9:
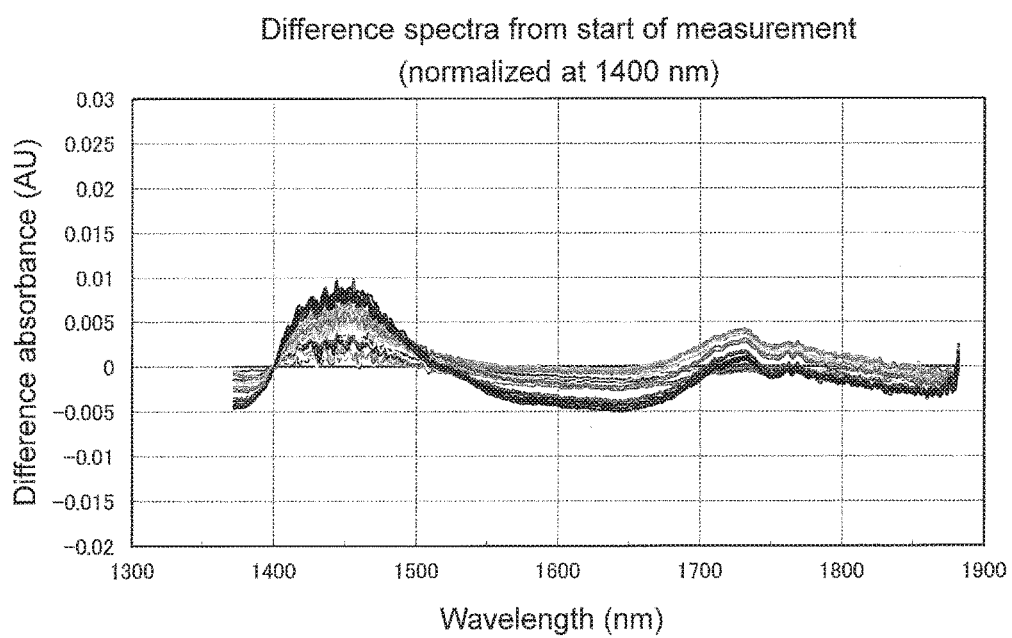
FIG. 9 is a diagram in which a change over time in the measured difference spectrum is plotted.

In FIG. 9, about 30 difference spectra obtained by subtracting the reference spectrum from the measurement spectra shown in FIG. 8 and normalizing the resulting spectra based on absorbances at 1400 nm are plotted. FIG. 6 described above is a diagram illustrating the spectra of biological components normalized at 1400 nm that are to be used to synthesize the difference spectrum and are. In FIG. 6, a thick line indicates the spectrum of the water 101, a thin line indicates the spectrum of the glucose component 102, and a dashed line indicates the spectrum of the fat component 103. In addition, a dotted line indicates the spectrum of a protein component 116.

The change over time in the difference spectrum shown in FIG. 9 includes characteristic absorbance peak changes near 1450 nm and 1727 nm. When compared with the shapes of the spectra of the biological components shown in FIG. 6, it is estimated that in the change in the spectrum measured for the skin tissue in this embodiment shown in FIG. 9, the biological components, that is, the water 101 and the fat component 103, having specific absorption peaks corresponding to the above-described two wavelengths are large factors in this change over time. (The spectra of the biological components shown in FIG. 6 are normalized at 1400 nm in the same manner as the difference spectra.)

Regarding the glucose component 102, the concentration thereof changed by 100 mg/dL in the experiment, but the change in the spectral shape caused by the glucose component 102 is not clearly shown in the difference spectra in FIG. 9.

In this manner, in the measurement of a glucose concentration in a living organism, which is mainly described in this application, the change in signals from disturbance components such as water and fat is bigger than the change in signals from glucose, and this is one of the reasons why the detection of glucose is difficult.

In this embodiment, the change over time in the glucose concentration in the skin tissue is estimated by synthesizing difference spectra as shown in FIG. 9 using the respective absorbance spectra of the biological components such as the water 101, the glucose component 102, and the fat component 103 shown in FIG. 6, and by determining the blood glucose level using the concentration index of the glucose component used in synthesizing, and this is an application of a spectroscopic quantification method called CLS (classical least squares).

An object of this embodiment is to quantify a biological component with a small spectral change such as the change in the glucose concentration in a living organism, and it is possible to accurately quantify the variation from the reference spectrum by applying the above-mentioned CLS method to the amount of change from the reference spectrum, that is, the difference spectrum.

A synthesis method utilizing a general determinant method used in the CLS method can be used in the synthesis of the difference spectrum. Therefore, a matrix theory method can be used to perform the synthesis using the entire wavelength range of the measurement spectrum as well as the synthesis using a picked-up useful wavelength or wavelength range. For example, it is possible to obtain a solution by using a combination of a transposed matrix and an inverse matrix as generally used in a spectral analysis without using a square matrix such as the square matrix as described in this embodiment.

This embodiment is an example in which a change in the baseline caused by scattered change is small. The difference spectrum was synthesized by producing a square matrix with three rows and three columns based on the absorbance at 1450 nm, which is a specific absorption wavelength of water 101, the absorbance at 1600 nm, which is a specific absorption wavelength of the glucose component 102, and the absorbance at 1727 nm, which is a specific absorption wavelength of the fat component 103, in the respective spectra of the biological components shown in FIG. 6, and performing computation using a determinant.

As described above, FIG. 7 is a diagram illustrating a determinant (three rows and three columns) to be used to synthesize a difference spectrum. As shown in FIG. 7, difference absorbances at the respective wavelengths are obtained by multiplying the square matrix, which was produced based on the absorbances of the spectra of the biological components at the respective wavelengths, by concentration indices (changes from the concentration index at the time of the measurement of the reference spectrum) of the respective components. In this formula, W represents a water component, G represents a glucose component, F represents a fat component, C represents a component concentration index, $\Delta OD$ represents a difference absorbance, and a subscript on the right side represents a corresponding wavelength or a component. For example, W1450 represents an absorbance of a water component at 1450 nm, and CW represents a concentration index of a water component.

A square matrix has an inverse matrix, and therefore, when the right and left terms of the determinant are multiplied using the calculated inverse matrix in the same direction, the concentration indices of the respective components can be determined as the products of the inverse matrix and the difference spectra.

Synthesizing the difference spectrum using the spectra of the biological components in this manner makes it possible to synthesize a spectrum in which the influence of disturbance is suppressed or to produce a calibration curve without collecting data by performing a preparatory experiment that is generally used in a near-infrared spectroscopic method.

Producing a square matrix using the specific absorption wavelengths of the spectra of the biological components makes it possible to accurately estimate a concentration by performing a simple arithmetic operation. Also, since the measurement can be performed at several wavelengths, it is possible to develop a small and inexpensive measurement device using an LED or a semiconductor laser.

In Example 1, a blood glucose level was estimated according to the procedure shown in the flowchart described in FIG. 3.

The measurement probe 9 is attached to the surface of the skin using a double-sided adhesive tape, and the measurement is started after a lapse of 45 minutes since then.

In step S1 (indicated as S1 in FIG. 3), a measurement spectrum at the start of the measurement is used as a reference spectrum.

In step S2 (indicated as S2 in FIG. 3), a spectrum is measured.

In step S3 (indicated as S3 in FIG. 3), a differential spectrum between the reference spectrum and each measurement spectrum is determined, and a difference spectrum is calculated.

In step S4 (indicated as S4 in FIG. 3), the obtained difference spectrum is synthesized based on the spectra of the biological components.

In step S5 (indicated as S5 in FIG. 3), the concentration index CG of the glucose component is calculated. Step S4 and step S5 correspond to an example of a concentration index calculation step.

In step S6 (indicated as S6 in FIG. 3), an estimated blood glucose level is obtained by converting the concentration index CG of the glucose component into a blood glucose level. Step S6 corresponds to an example of a glucose concentration calculation step.

In step S7 (indicated as S7 in FIG. 3), the operations after step S2 are repeated every 5 minutes until the measurement is finished.

Figure 10:
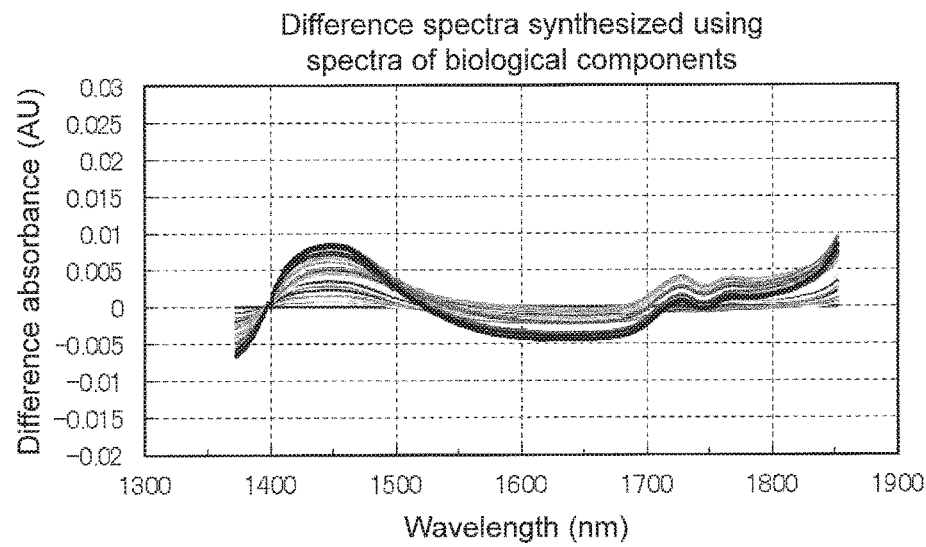
FIG. 10 is a diagram in which a change over time in the synthesized difference spectrum is plotted.

With the above-mentioned method, the component concentration indices CW, CG, and CF are calculated with respect to each of the difference spectra measured every 5 minutes, and the difference spectra are synthesized using the component spectra and the component concentration indices as shown in FIG. 10. Here, the reason why CW, CG, and CF are referred to as "component concentration indices" is that CW, CG, and CF have only relative meanings with respect to the actual concentrations because spectra obtained by taking the maximum values and minimum values of the spectra of the biological components as 1 and 0, respectively, and normalizing the spectra of the biological components at 1400 nm are used in the synthesis of the difference spectra. In order to calculate a blood glucose level, it is necessary to multiply the estimated concentration index CG of the glucose component by a conversion factor. This conversion factor is experimentally determined such that the variation in the concentration index CG of the glucose component matches the variation in the actual blood glucose level. That is, the conversion factor is determined in advance by comparing the blood glucose level measured using a simple blood glucose monitor for measuring collected blood and the concentration index CG.

When the actually measured difference spectra shown in FIG. 9 and the change over time in the synthesized difference spectra shown in FIG. 10 are compared, the changing shapes of the spectra shown in both FIG. 9 and FIG. 10 match well each other, and thus it can be seen that favorable synthesis of spectra can be performed with the above-described method.

Figure 11:
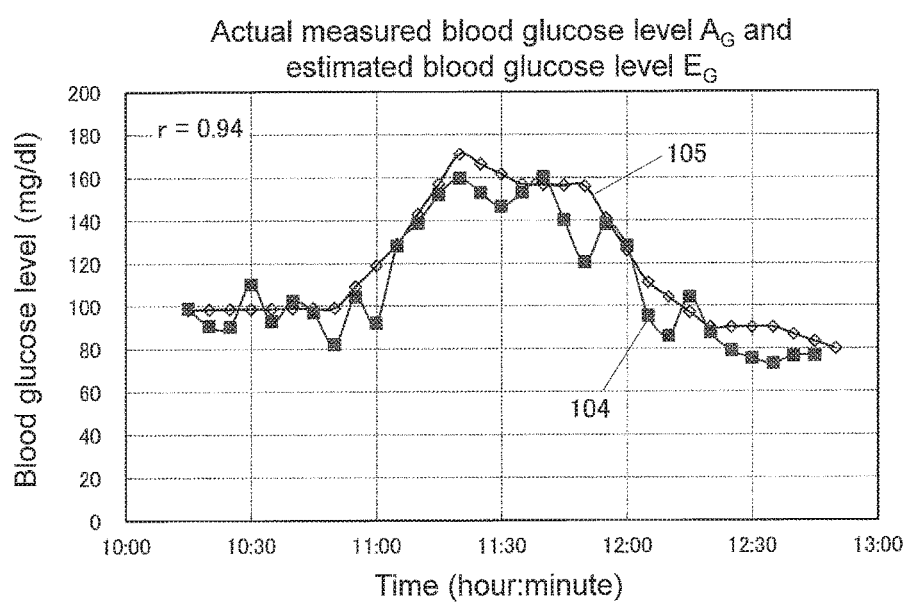
FIG. 11 is a diagram illustrating a change over time in an actual measured blood glucose level and a change over time in an estimated glucose concentration.

The value of the concentration index CG of the glucose G here is converted into the change in the blood glucose level, a constant term is determined such that an estimated blood glucose level 104 at the start of the measurement (at the time of the measurement of a reference spectrum) matches an actual measured blood glucose level 105, and thus the blood glucose level is estimated. FIG. 11 shows a graph of the estimated blood glucose level.

As shown in FIG. 11, in this embodiment, the correlation coefficient between the estimated blood glucose level 104 determined by synthesizing the spectrum and the actual measured blood glucose level 105 was 0.94.

A conversion factor (α) for converting a concentration index into a glucose concentration was 0.00005 (mg/dL)–1. The actual measured blood glucose level (V0) at the start of the measurement was 98 mg/dL.

Accordingly, it was found from the results from Example 1 that the glucose concentration measurement device of this embodiment can be used to obtain the same change in the blood glucose level as the measurement values obtained by actually measuring collected blood.

As shown in this embodiment, in an example in which a so-called change in the baseline is small, the change in the blood glucose level can be accurately estimated by synthesizing the difference spectra based on a simple determinant using the specific absorption wavelengths of the biological components. Therefore, it is possible to accurately estimate a blood glucose level under the measurement condition that the change in the baseline is not large.

For example, it is also possible to use the method of this embodiment in the estimation of a blood glucose level in the case where the change in the baseline is small while a change in the difference spectrum is observed. The changes in the absorbances at wavelengths of 1550 to 1680 nm are used to determine whether or not the baseline of the difference spectrum has grown, and if the baseline has not grown, it is possible to measure a blood glucose level using the above-mentioned algorithm.

In this embodiment, the absorbance at 1650 nm did not exceed 0.001, and therefore, it was determined that the growth of the baseline was small.

Also, it is useful to measure a spectrum in a living organism under the measurement condition that the baseline is unlikely to vary. As described above, the appropriate growth of the spectrum of the water component suppresses an increase in the baseline, and therefore, it is desirable to perform processing to promote the growth of the water component in a portion at which the measurement probe is in contact with the skin. For example, it is also useful to set the contact pressure to be slightly high or set the environmental temperature to be high.

Embodiment 2

Hereinafter, a glucose concentration measurement device and a method for quantifying a glucose concentration of Embodiment 2 according to the present invention will be described.

This Embodiment 2 differs from Embodiment 1 in that the synthesis of a spectrum is performed in consideration of a baseline variation.

2-1. Baseline Variation

First, a baseline variation will be described.

In the Embodiment 1, in order to reduce the influence of the baseline variation caused by scattering or the like, the actually measured spectra and the component spectra were normalized based on the absorbances at 1400 nm as described above, and the synthesis of a spectrum was performed to obtain the normalized difference spectra. However, as described in the drawbacks of the CLS method, if the estimation of unexpected disturbance factors, particularly the number of components, has been misread, the quantification accuracy will decrease. In particular, in an example in which not the biological components but a so-called change in the baseline significantly affects the change in the difference spectrum, disturbance such as a baseline variation cannot be sufficiently removed by only the normalization at 1400 nm.

Figure 12:
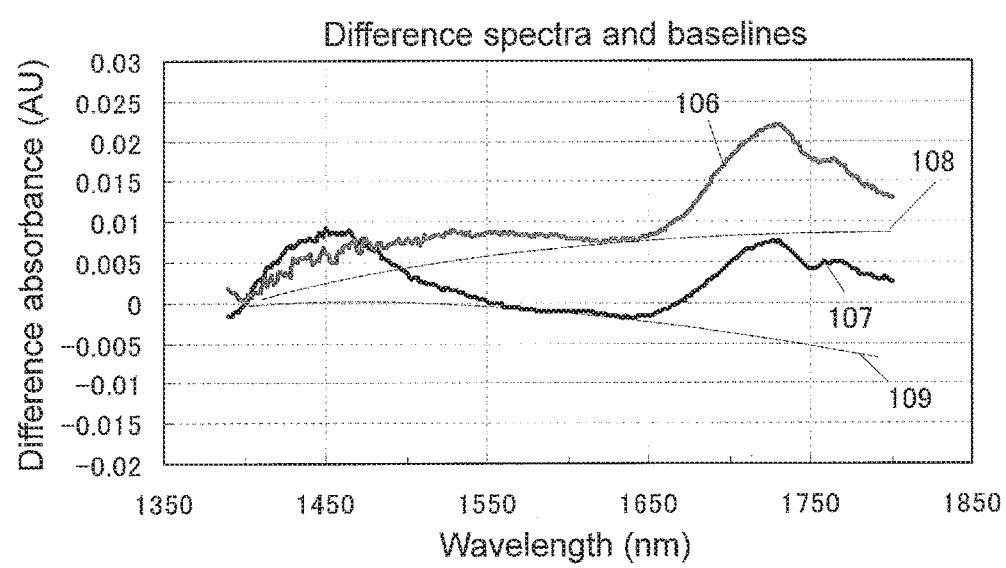
FIG. 12 is an explanatory diagram of difference spectra normalized at 1400 nm and baselines.

FIG. 12 is a diagram illustrating difference spectra and baselines.

A difference spectrum 106 and a difference spectrum 107 shown in FIG. 12 are spectra after a lapse of about 3 hours from which the measurement was started in experiments performed on different dates and times. As shown in FIG. 12, the difference spectrum 106 is significantly affected by a change in the scattering coefficient of skin tissue, and a baseline 108 increases over time. On the other hand, the difference spectrum 107 is not significantly affected by a change in the scattering coefficient of skin tissue, and a baseline 109 decreases over time. It can be inferred that the decrease in a baseline is caused by the influence of water on the scattering coefficient because a large variation having a peak at 1450 nm appears.

Incidentally, the wavelength characteristic of a scattering coefficient generally decreases monotonously as the wavelength increases, but a diffuse reflectance spectrum as in this embodiment has a characteristic that the absorbance increases monotonously as the wavelength increases.

It is thought that such a difference in behavior of the change in the baseline due to the change in the scattering coefficient is caused by skin factors such as color, portion, thickness, water content, surface roughness and temperature of a skin subjected to the spectral measurement, and environmental factors such as temperature and humidity, and these factors are non-negligible error factors in the measurement of glucose in the skin tissue. Therefore, it is no exaggeration to say that when the synthesis of spectra is performed using the CLS method, the quantification accuracy depends on whether or not the behavior of the baseline has been distinguished.

In the near-infrared spectroscopy, a method in which a so-called change in the baseline caused by the change in the scattering coefficient is removed by performing differential processing is well known and is effective in the detection of a component having a clear absorption peak. However, as shown in FIG. 6, when a component such as glucose whose spectrum has a loosely broad shape having no clear absorption peak is detected, the differential processing is not very appropriate. Therefore, in this embodiment, the differential processing is not performed. Also, MSC (multiplicative scatter correction) processing is frequently used to remove the influence of the baseline and can be applied to this example, but is not used in this embodiment.

As described above, since the spectrum of glucose has a broad shape having no clear peak as shown in FIG. 6, in the analysis of a glucose concentration in a living organism, it is difficult to analytically distinguish the spectrum of glucose from the change in the baseline (baseline 108 shown in FIG. 12) caused by a scattered change and the like, and estimation errors are likely to occur. Accordingly, it is necessary to take some measures for distinguishing the spectrum of glucose and the change in the baseline in order to favorably estimate a glucose concentration.

Therefore, in this embodiment, in order to distinguish the change in the spectrum of the glucose component and the change in the spectrum of the baseline included in the difference spectrum, the measurement accuracy was improved by synthesizing the difference spectrum not using the change in the baseline as an independent factor but using an imaginary spectrum obtained by combining the change in the spectrum of the fat component and the change in the baseline, which are thought to be generated by the same mechanism including a scattered change, as a component spectrum.

It will be explained that the change in the spectrum of the fat component and the change in the baseline are generated by the same mechanism including a change in the scattering coefficient, which is mentioned above. It is thought that the increase in peak value at 1727 nm indicating the characteristic wavelength of the spectrum of the fat component in the difference spectra shown in FIG. 9 and FIG. 12 does not indicate an increase in the amount of fat in the tissue. The reason is that an increase in a volume fraction of a fat tissue and an increase in a fat concentration in blood are thought to cause the increase in the amount of fat, but the fat tissue is unlikely to increase in several hours when a blood glucose level is measured. Also, with regard to the fat concentration in blood, the peak at 1727 nm starts to grow before the oral load is ingested, and in the meantime, the fat concentration in blood hardly changes.

Therefore, it should be understood that the growth of (increase in) the peak value at 1727 nm in this experiment is caused by a generation factor other than the substantial amount of fat. It is thought that the generation factor is the change in the scattering coefficient of the surface of the skin, which is in contact with the light receiving-side optical fiber 19 and the light-emitting fibers 20.

The light receiving-side optical fiber 19 and the light-emitting fibers 20 are in contact with the skin at the start of the measurement. The surface of the skin is relatively uneven due to the presence of skin depressions and skin ridges. The unevenness of the surface of the skin causes large light scattering at the surface of the skin, and the amount of light entering the skin decreases. The uneven structure of the surface of the skin, which is in contact with the light receiving-side optical fiber 19 and the light-emitting fibers 20, turns into an even surface over time. This causes light scattering at the surface of the skin to be small, and thus the amount of light entering the inside of the skin increases. When the amount of light increases, the amount of light reaching the subcutaneous tissue (fat layer) in a deep portion of the skin increases, and the peak at 1727 nm grows. When the scattering coefficient of the surface of the skin decreases, light that passes through a light path bypassing the surface of the skin tissue decreases, and thus the baseline increases.

Therefore, it can be explained that the change in the spectrum of the fat component and the change in the baseline are generated by the same mechanism including a change in the scattering coefficient.

2-2. Glucose Concentration Measurement Device

Figure 13:
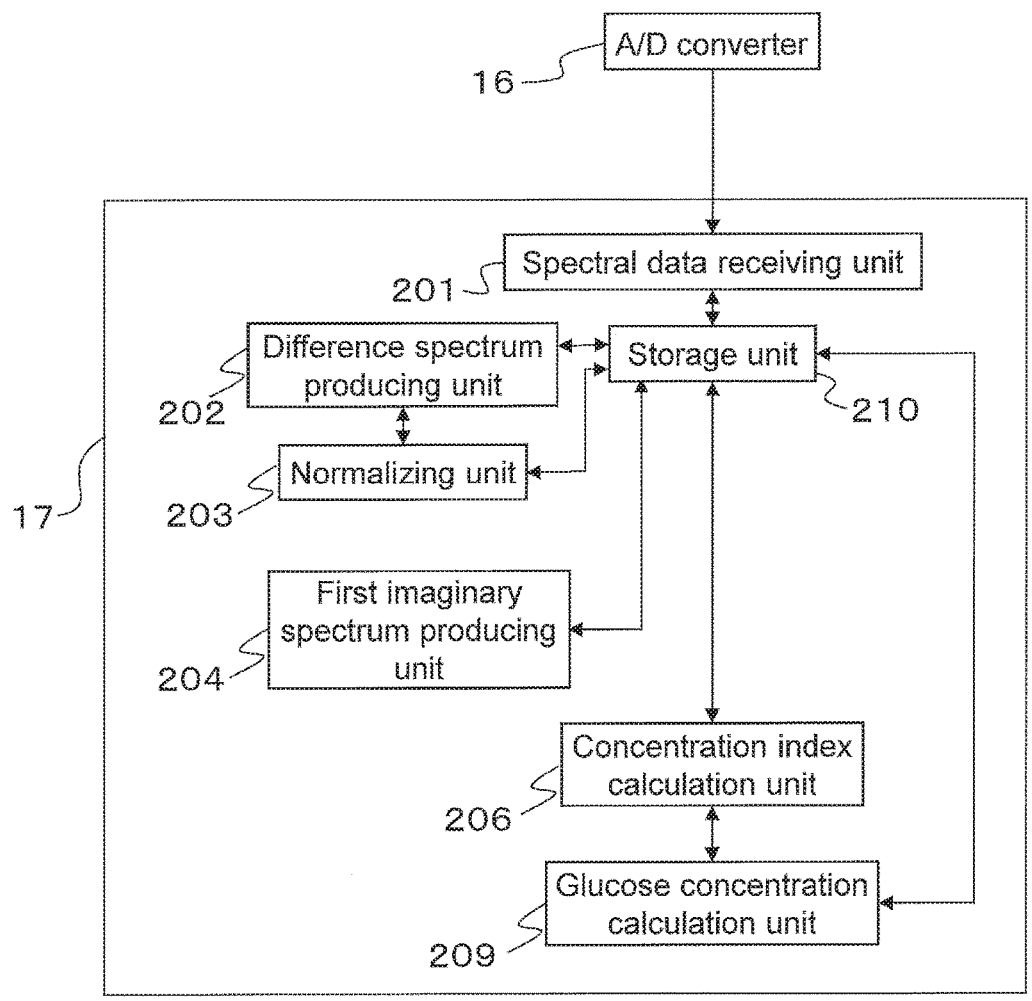
FIG. 13 is a block diagram illustrating a configuration of an arithmetic device of a glucose concentration measurement device of Embodiment 2.

FIG. 13 is a block diagram illustrating a control configuration of the arithmetic device 17 of the glucose concentration measurement device of this Embodiment 2.

As shown in FIG. 13, the arithmetic device 17 of the glucose concentration measurement device of this embodiment includes the spectral data receiving unit 201, the difference spectrum producing unit 202, the normalizing unit 203, a first imaginary spectrum producing unit 204, the concentration index calculation unit 206, the glucose concentration calculation unit 209, and a storage unit 210.

The spectral data receiving unit 201 and the difference spectrum producing unit 202 have the same configurations as those of Embodiment 1, and therefore, description thereof will be omitted.

The first imaginary spectrum producing unit 204 includes an averaging means, the averaging means performs smoothing processing on the normalized difference spectrum, and a first imaginary spectrum is produced using, in that spectrum, the change in the baseline and the change in the spectrum of the fat component.

The concentration index calculation unit 206 uses the first imaginary spectrum, and spectral data of a water component and spectral data of a glucose component stored in the storage unit 210 to synthesize the difference spectrum obtained by subtracting the reference spectrum from the spectrum obtained at the time of the measurement of a glucose concentration and normalizing the resulting spectrum, and calculates a concentration index CG.

The glucose concentration calculation unit 209 calculates a glucose concentration by matching the glucose concentration at the time of the measurement of a reference spectrum with the actual measured blood glucose level at that time, converting the value of the corrected concentration index CG into the change in the glucose concentration, and adding the converted change in the glucose concentration to the glucose concentration at the time of the measurement of a reference spectrum.

The conversion factor to be used to convert a concentration index CG value into a change in the glucose concentration, the spectral data at the time of the measurement of a glucose concentration, the reference spectral data, the difference spectrum, the difference spectrum normalized at 1400 nm, the first imaginary spectrum data, the spectral data of the water component, the spectral data of the glucose component, and the like are stored in the storage unit 210.

2-3. Method for Measuring Blood Glucose Level

A procedure to measure a blood glucose level of a person to be subjected to blood glucose measurement using the above-described glucose concentration measurement device will be described.

Figure 14:
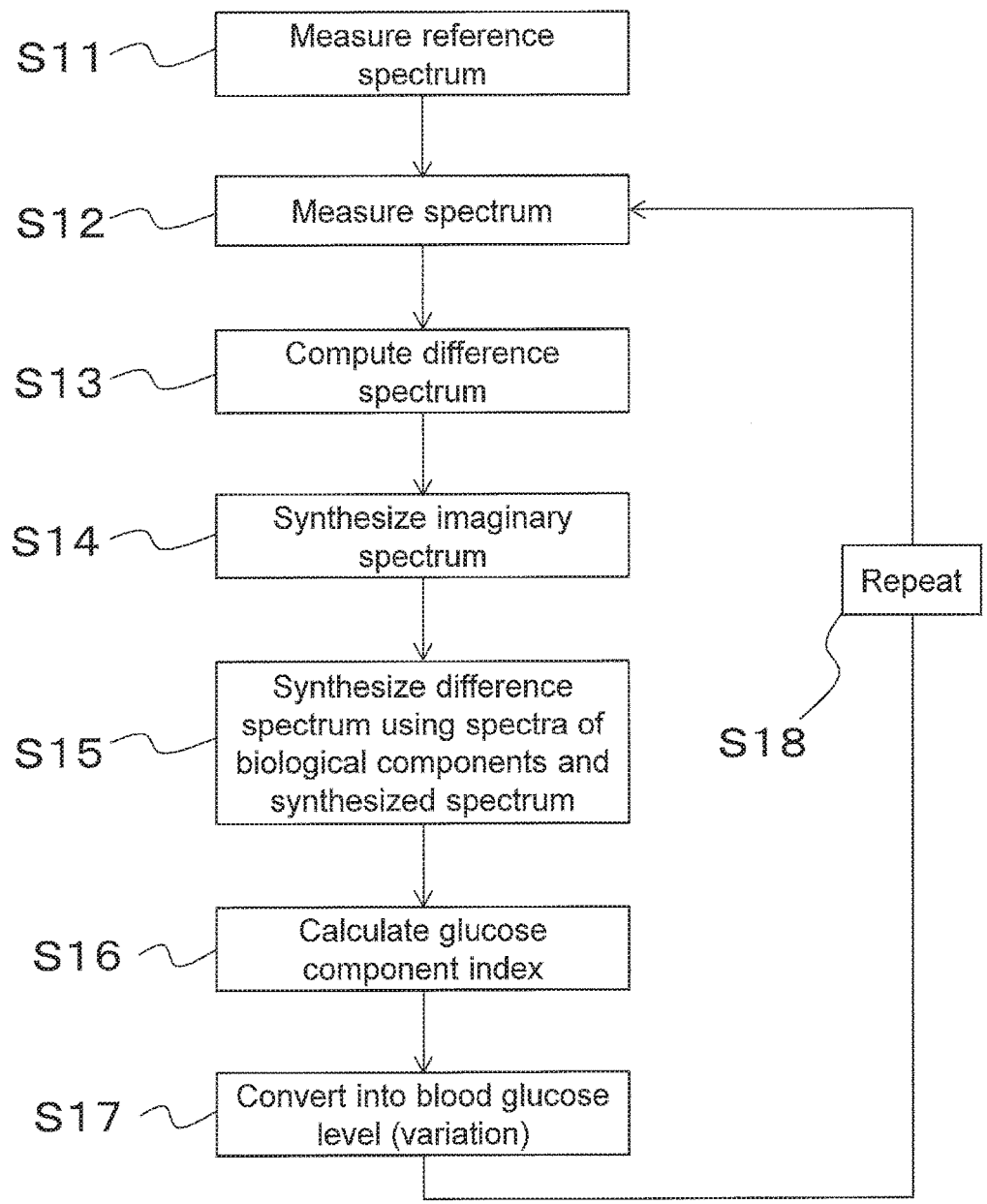
FIG. 14 is a flowchart illustrating a measurement procedure in the Embodiment 2.

FIG. 14 is a flowchart illustrating a method for quantifying a blood glucose level of this Embodiment 2. Steps S11, S12, and S13 of the method for measuring a glucose concentration of this Embodiment 2 are the same as those of Embodiment 1, and therefore, description thereof will be omitted.

Figure 15:
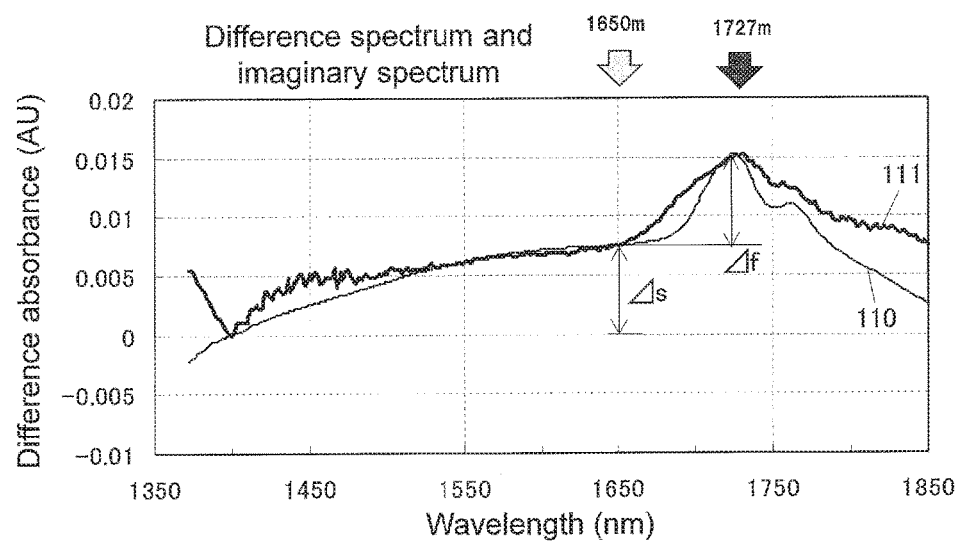
FIG. 15 is an explanatory diagram of a method for producing an imaginary spectrum synthesized in each measurement.

(1) In the method for measuring a glucose concentration of this Embodiment 2, the first imaginary spectrum producing unit 204 produces an imaginary spectrum using, in the measurement spectrum, the characteristic wavelength of a baseline variation and the characteristic wavelength of the spectrum of the fat component in step S14 subsequent to step S13. The first imaginary spectrum producing unit 204 having a smoothing means produces the imaginary spectrum according to the following procedure. This step S14 corresponds to an example of a first imaginary spectrum producing step.

a) An imaginary spectrum is determined by adding together fat and the change in the baseline in each measurement. FIG. 15 is a diagram illustrating an imaginary spectrum 110. As shown in FIG. 15, the imaginary spectrum 110 is determined by adding together fat and the change in the baseline in each measurement. The addition is performed by smoothing both the baseline and the spectrum of the fat component based on the change in the baseline by $\Delta s$ that is a change in the absorbance at 1650 nm, which represents the characteristic of the baseline of the difference spectrum, and the change in the fat spectrum by $\Delta f$ that is a change in the difference between absorbances at 1650 nm and 1727 nm which is the specific absorption wavelengths of the fat component.

b) A specific calculating method in the above-mentioned smoothing will be described below. In this embodiment, Δs, which is a change in an absorbance at 1650 nm and Δf, which is a change in the difference between absorbances at 1727 nm and 1650 nm, in each of the difference spectra, are not used with raw date but are used with values obtained by reducing the changes using the averaging means performing the smoothing processing. The smoothing in this embodiment was performed according to the following procedure.

i) Two indices (Δs0, Δf0) at the time of the measurement of a reference spectrum are used as references.

ii) Changes (Δsn, Δfn) in a measurement spectrum from the reference spectrum are calculated every 5 minutes (n is the number of measurements).

iii) A change until the time point at which the measurement is performed and the absorbance at the time of the measurement of a reference spectrum are added together one after another and divided by the number of values added.

(Δs0+Δs1+Δs2+ . . . +Δsn)/(n+1)

(Δf0+Δf1+Δf2+ . . . +Δfn)/(n+1)

iv) The obtained values are used as smoothed values. Hereinafter, a value obtained by the above-mentioned averaging (smoothing) means are referred to as "integration average". An imaginary spectrum is produced by adding the baseline spectrum and the fat spectrum at a ratio of the two integration average value.

(2) The concentration index calculation unit 206 synthesizes a difference spectrum using at least the spectrum of the water component, the spectrum of the glucose component, and the imaginary spectrum (step S15), and thus the concentration index CG of the glucose component is calculated (step S16). A determinant of a square matrix based on the absorbances at the characteristic wavelengths of the components is used in the synthesis. Step S15 and step S16 correspond to an example of a concentration index producing step.

The synthesis of a spectrum is performed according to the following procedure.

a) A square matrix with three rows and three columns is produced based on the absorbances at 1450 nm, which is the specific absorption wavelength of the water 101, the absorbances at 1600 nm, which is the specific absorption wavelength of the glucose component 102, and the absorbances at 1727 nm (see FIG. 15), which is the specific absorption wavelength of the fat component, as the specific absorption wavelength of the imaginary spectrum, in the respective spectra of the biological components shown in FIG. 6.

b) Difference absorbances at the respective wavelengths are obtained by multiplying the square matrix, which was produced based on the absorbances of the spectra of the biological components at the respective wavelengths, by concentration indices (changes from the concentration index at the time of the measurement of a reference spectrum) of the respective components.

c) A square matrix has an inverse matrix, and therefore, when the right and left terms of the determinant are multiplied using the calculated inverse matrix in the same direction, the concentration indices of the respective components can be determined as the products of the inverse matrix and the difference spectra.

(3) The concentration index calculation unit 206 calculates a blood glucose level using the above-mentioned concentration index of the glucose component (step S17) in the same manner as in Embodiment 1. A conversion factor α that is determined in advance is used to calculate a blood glucose level using the glucose concentration index. That is, the glucose concentration Vt is calculated according to an equation Vt=V0+α×CG. This step S17 corresponds to an example of a glucose concentration calculation step.

It should be noted that since the spectral measurement of the skin tissue is performed every 5 minutes, the blood glucose level is continuously estimated every 5 minutes (step S18).

As described above, in this Embodiment 2, when the concentration index CG of the glucose component is determined, the imaginary spectrum determined using the baseline spectrum and the spectrum of the fat component is used instead of the spectrum of the fat component in Embodiment 1.

Next, the glucose concentration measurement device and the method for quantifying a glucose concentration according to this Embodiment 2 will be described in detail by way of Example 2, which is an experimental example.

2-4. Example 2

In this experiment, in the same manner as in Example 1, a glucose load was provided orally to a healthy subject, and the change in the blood glucose level (change in the glucose concentration in a biological tissue) was quantified.

The blood glucose level is estimated according to the procedure shown in the flowchart as shown in FIG. 14 described in Embodiment 2 above. The measurement is started after a lapse of 45 minutes from which the measurement probe 9 was attached.

In step S11 (indicated as S11 in FIG. 14), a measurement spectrum at the start of the measurement is set to be a reference spectrum.

In step S12 (indicated as S12 in FIG. 14), a spectrum is measured.

In step S13 (indicated as S13 in FIG. 14), a differential spectrum between the reference spectrum and each measurement spectrum is determined, and difference spectra are calculated.

In step S14 (indicated as S14 in FIG. 14), an imaginary spectrum is produced using the change in the baseline and the change in the spectrum of the fat component, which have undergone the smoothing processing. Step S14 corresponds to an example of a first imaginary spectrum producing step.

In step S15 (indicated as S15 in FIG. 14), the difference spectrum obtained in step S13 is synthesized using the spectra of the biological components and the imaginary spectrum.

In step S16 (indicated as S16 in FIG. 14), the concentration index CG of the glucose component is calculated. Step S15 and step S16 correspond to an example of a concentration index producing step.

In step S17 (indicated as S17 in FIG. 14), an estimated blood glucose level is obtained by converting the glucose index into a blood glucose level. Step S17 corresponds to a glucose concentration calculation step.

In step S18 (indicated as S18 in FIG. 14), the operations after step S12 are repeated every 5 minutes until the measurement is finished.

Figure 16:
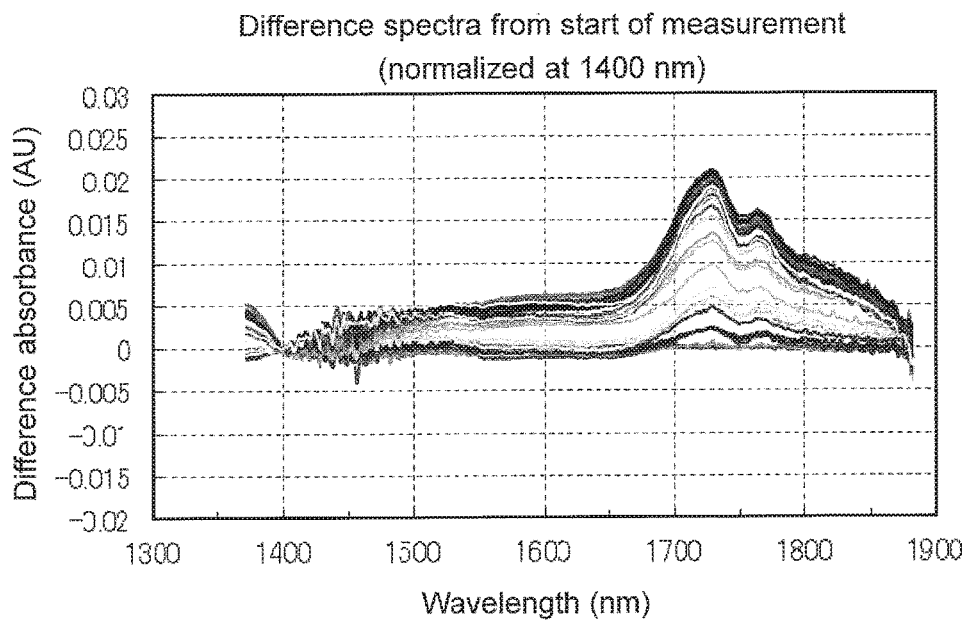
FIG. 16 is a diagram in which a change over time in the measured difference spectrum is plotted.

FIG. 16 is a diagram illustrating the change over time in the difference spectrum obtained by using the spectrum of the skin tissue at the start of the measurement as a reference to determine the difference from each of the measurement spectra. The difference spectra shown in FIG. 16 are normalized based on the absorbances at 1400 nm as described above.

As is clear from the difference spectra shown in FIG. 16, in the change in the spectrum of the skin tissue in this glucose load experiment, the changes in the characteristic absorption peak at 1727 nm and the so-called increase in a baseline that is an increase in an absorbance depending on an increase in a wavelength over time are observed. Therefore, the change over time in the difference spectrum suggests that in this embodiment, the fat component 103 and the change in the absorbance caused by the change in the baseline are large disturbance factors.

In this embodiment, in order to calculate the change over time in the glucose concentration in the skin tissue, the difference spectra shown in FIG. 16 were synthesized using the respective spectra of the water component and the glucose component shown in FIG. 6 and the imaginary spectrum 110 shown in FIG. 15.

As shown in FIG. 15, the imaginary spectrum 110 is determined by adding together fat and the change in the baseline in each measurement. The addition is performed by adding together the spectra of the baseline and the fat component in corresponding amounts based on the change in the baseline by $\Delta s$ that is a change in the absorbance at 1650 nm, which represents the characteristic of the baseline of the difference spectrum 111, and the change in the fat spectrum by $\Delta f$ that is a change in the difference between absorbances at 1727 nm and 1650 nm, which are the specific absorption wavelengths of the fat component. In this embodiment, a monotonously increasing curve (baseline 108) normalized at 1400 nm as shown in the difference spectrum 106 in FIG. 12 was used as the change in the baseline.

The wavelengths are not limited to 1727 nm, which is the specific absorption wavelength of the fat component, and 1650 nm, which is the characteristic wavelength of the change in the baseline, and may be selected from wavelengths around these wavelengths. When the influence of the change in the concentration of the glucose component is reduced, even if the difference in an absorbance at a wavelength of 1550 nm to 1680 nm is used as the characteristic wavelength of the change in the baseline, the same effect can be obtained.

In this embodiment, $\Delta s$, which is a change in an absorbance at 1650 nm in each of the difference spectra, and $\Delta f$, which is a change in the difference between absorbances at 1727 nm and 1650 nm, are used with raw data, but are used with values obtained by reducing the changes using the averaging means performing the smoothing processing without using raw data. The smoothing in this embodiment was performed according to the following procedure.

(1) Two indices ($\Delta s0$, $\Delta f0$) at the time of the measurement of a reference spectrum are used as references 0.

(2) Changes ($\Delta sn$, $\Delta fn$) in a measurement spectrum from the reference spectrum are calculated every 5 minutes (n is the number of measurements).

(3) A change until the time point at which the measurement is performed and the absorbance at the time of the measurement of a reference spectrum are added together and divided by the number of values added.

$$(\Delta s0+\Delta s1+\Delta s2+ \ldots +\Delta sn)/(n+1)$$

$$(\Delta f0+\Delta f1+\Delta f2+ \ldots +\Delta fn)/(n+1)$$

(4) The obtained values are used as smoothed values.

Hereinafter, a value obtained by the above-mentioned averaging (smoothing) means are referred to as "integration average".

The reason why the smoothing processing is performed on $\Delta s$, which is a change in an absorbance at 1650 nm and $\Delta f$, which is a change in the difference between absorbances at 1727 nm and 1650 nm, in each of the difference spectra, is that the spectrum of the glucose component also includes large absorptions at 1650 nm and 1727 nm as is clear from the component spectra shown in FIG. 6, and that the variation in the glucose concentration is superposed onto the raw data at these two wavelengths. Therefore, it is intended to separate the change in glucose and change in the baseline, which have different time constants, by performing the smoothing processing on the values measured over time and to reduce the influence of glucose superposed onto the change in the baseline. That is, it is intended to separate the blood glucose level, which changes in about 2 hours in a healthy person, and the change in the baseline, which is caused by the change in the scattering coefficient and changes over not less than 4 hours to several hours, based on the difference in a time constant.

In other words, it can be said that in the estimation of a blood glucose level in this embodiment, the amount of information to be used in the estimation of a blood glucose level is increased by adding information obtained from the change over time to the spectral information including a wavelength and an absorbance, to improve the accuracy.

Although a Savitzky-Golay method, a Fourier transformation method, a regression approximation using an n-th curve, an averaging method, and the like are general methods for performing smoothing processing, a value obtained by integrating the difference absorbances at wavelengths of 1650 nm and 1727 nm and then dividing the sum of them by the number of integrations from the start of the measurement to that time point was used. The method used for the smoothing processing is not limited thereto, and any method may be used as long as the method can be used for the smoothing processing. Considering the characteristics of change in the blood glucose level in a healthy person, it is appropriate to perform the smoothing for not less than 2 hours, depending on the method.

In order to compare the effects of the smoothing processing, a change over time in a change 112 in an absorbance at 1650 nm, which represents the characteristic of the baseline of the difference spectrum, and a change over time in a value 113 obtained by subtracting an absorbance at 1650 nm from an absorbance at 1727 nm, which is the specific absorption wavelength of the fat component, are shown in FIG. 17(a) and FIG. 17(b). In the experiment of this embodiment, a glucose load was provided at around 14:30.

FIG. 17(a) is a diagram illustrating a state in which the change over time in the change 112 in an absorbance at 1650 nm and the change over time in a value 113 obtained by subtracting an absorbance at 1650 nm from an absorbance at 1727 nm have undergone the smoothing processing, and FIG. 17(b) is a diagram showing raw data that has not undergone the smoothing processing. In the change 112 in an absorbance at 1650 nm shown in FIG. 17(b) (raw data), which has not undergone the smoothing processing, a clear change corresponding to the variation in the blood glucose level caused by the glucose load can be observed as an increase in the absorbance. In contrast, in the change 112 in an absorbance at 1650 nm shown on the upper side, which has undergone the smoothing processing using the integration averages, the change, which is prominent around 14:30 in the raw data, is reduced. As described above, the smoothing processing reduces the influence of the change in the glucose concentration having a different time constant, and it can be seen that the smoothing processing such as the integration average method is effective.

Of course, when an imaginary spectrum is produced using data that has not undergone the smoothing processing and the glucose concentration index is estimated, since disturbance to be eliminated includes the glucose component factor, it is thought that the estimation cannot be performed more accurately compared with the case where the smoothing processing is performed.

Figure 18:
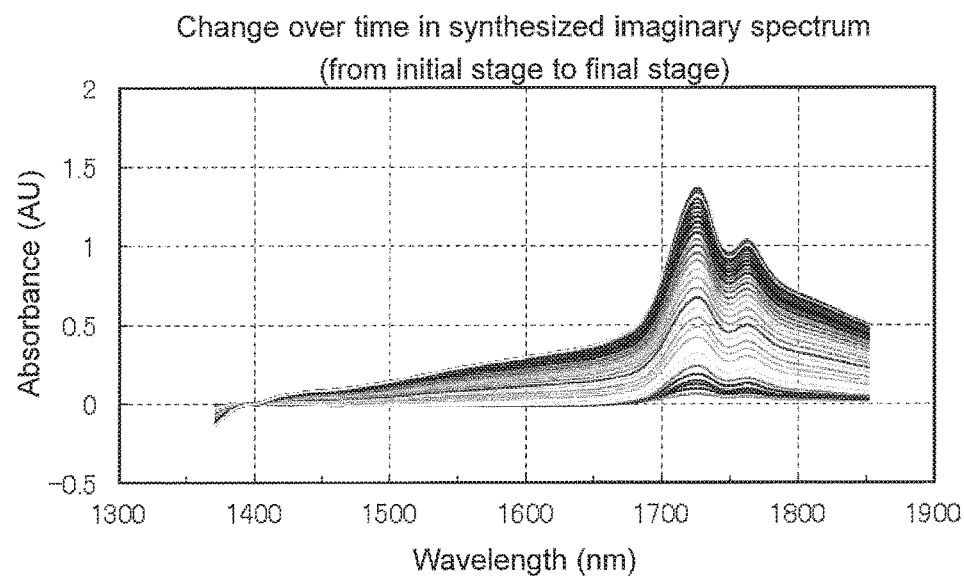
FIG. 18 is an explanatory diagram of a change over time in an imaginary spectrum synthesized in each measurement.

FIG. 18 is a diagram illustrating a change over time in the imaginary spectrum used in the glucose quantification in this embodiment (change from the initial stage to the final stage). It can be seen that the imaginary spectrum retains a relatively similar shape from the start of the measurement to the end of the measurement.

In this embodiment, the spectrum of the fat component in the determinant used in the Embodiment 1 (see FIG. 7) is replaced by the imaginary spectrum, and a glucose concentration is determined using the resulting determinant. In this method, if the shape of an imaginary spectrum that is synthesized using the fat and the baseline and is to be used to produce a matrix with three rows and three columns is determined (if the imaginary spectrum has a similar shape), the calculated value of the glucose concentration index is not affected by the size of the imaginary spectrum. That is, the method has a characteristic in which the calculated value of the glucose concentration index does not change even if the absorbances of the imaginary spectrum synthesized using the fat or the fat and the baseline are multiplied.

Figure 17:
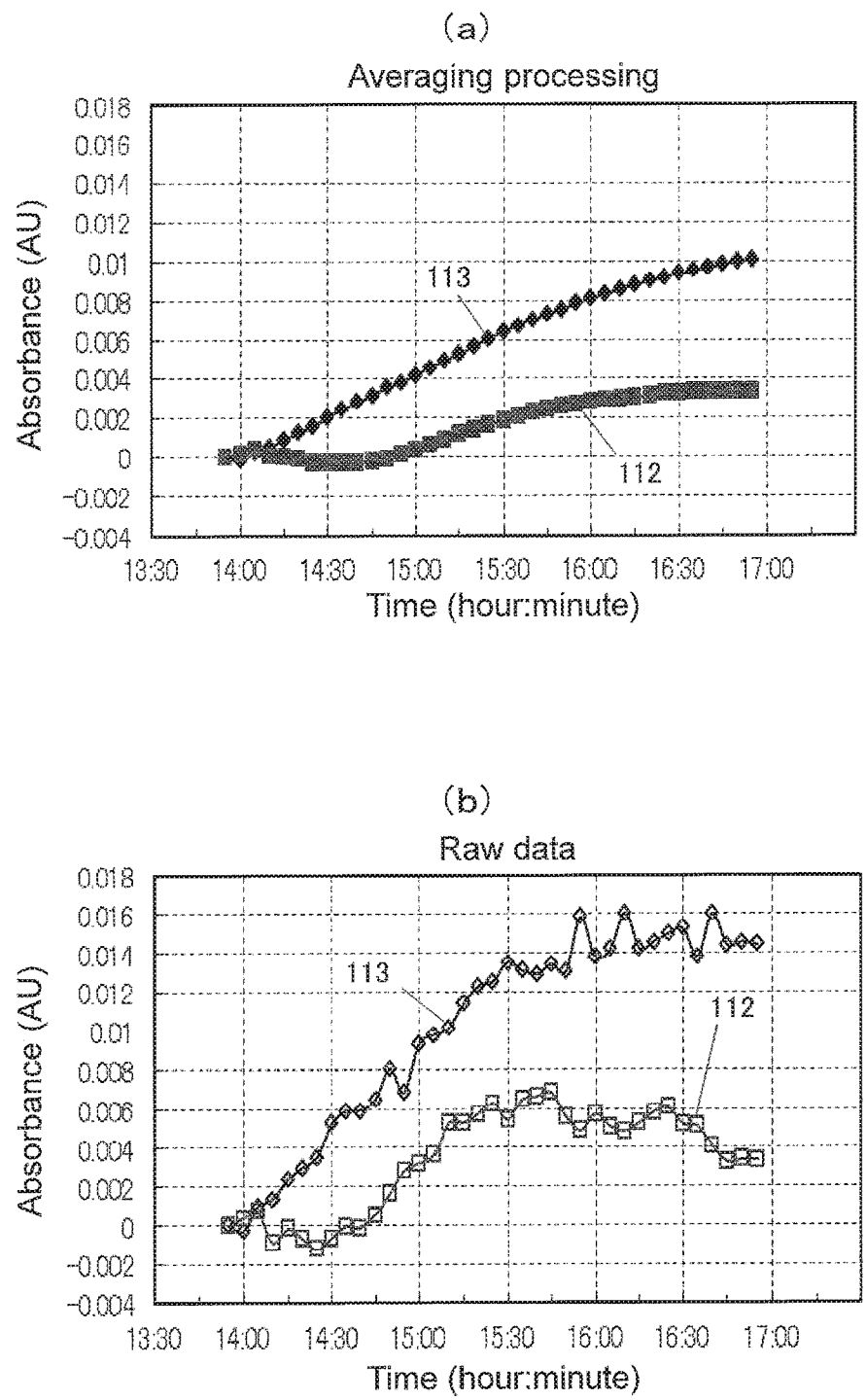
FIG. 17 shows diagrams for comparing indices when smoothing processing is performed (a) and is not performed (b).

That is, although the absolute values of the change in the baseline and the changes at 1650 nm and 1727 nm are reduced in FIG. 17 by performing the integration average method, if the imaginary spectrum obtained by adding together the fat and the baseline has the correct shape (similar shape), the glucose concentration index to be estimated is not affected.

Since the imaginary spectrum from which the change in the glucose concentration is removed can be obtained with the above-described smoothing processing, it is possible to accurately calculate the glucose concentration index using determinant computation, which will be described below.

It was clear from a glucose load experiment that was repeatedly performed on various subjects that the relationship between the fat peak and the so-called change in the baseline caused by the change in the scattering coefficient and the like was determined with various factors at the start of the spectral measurement to some extent and had a characteristic of continuing for a certain period of time.

However, although factors that determine the scattering state of the skin tissue, such as skin tissue factors including color, portion, thickness, water content, surface roughness, temperature, and the like of a skin tissue, and environmental factors including room temperature, humidity, and the like are considered as factors that determine the relationship between the fat peak and the so-called change in the baseline, it is not possible to clarify their contribution at present.

The measurement method of performing the measurement in a state in which a sensor is in intimate contact with the skin as this embodiment has a disadvantage in which the measurement spectrum is unstable because the surface of a skin to which a measurement probe is in contact is not sufficiently stable right after the start of the measurement and the amount of change in the obtained difference spectrum is small and thus easily affected by disturbance such as dark current caused by the measurement device. Therefore, it is desirable that the measurement is started after a lapse of a certain period of time from which the measurement probe is attached.

With regard to the change in the glucose concentration in the skin tissue in this embodiment, an absorbance at 1450 nm, which is the specific absorption wavelength of the water component, an absorbance at 1600 nm, which is the specific absorption wavelength of the glucose component, and an absorbance at 1727 nm, which is the specific absorption wavelength of an imaginary component, are extracted from the component spectra of water and glucose, and the imaginary spectrum, a square matrix with three rows and three columns is produced in each measurement, and then the difference absorbances at the respective wavelengths are obtained by multiplying this square matrix by the concentration indices (changes from the concentration at the time of the measurement of a reference spectrum) of the respective components. The square matrix produced in each measurement has an inverse matrix, and therefore, when the right and left terms of the upper formula are multiplied using the inverse matrix in the same direction, the concentration indices of the respective components can be determined as the products of the inverse matrix and the difference spectra.

Figure 19:
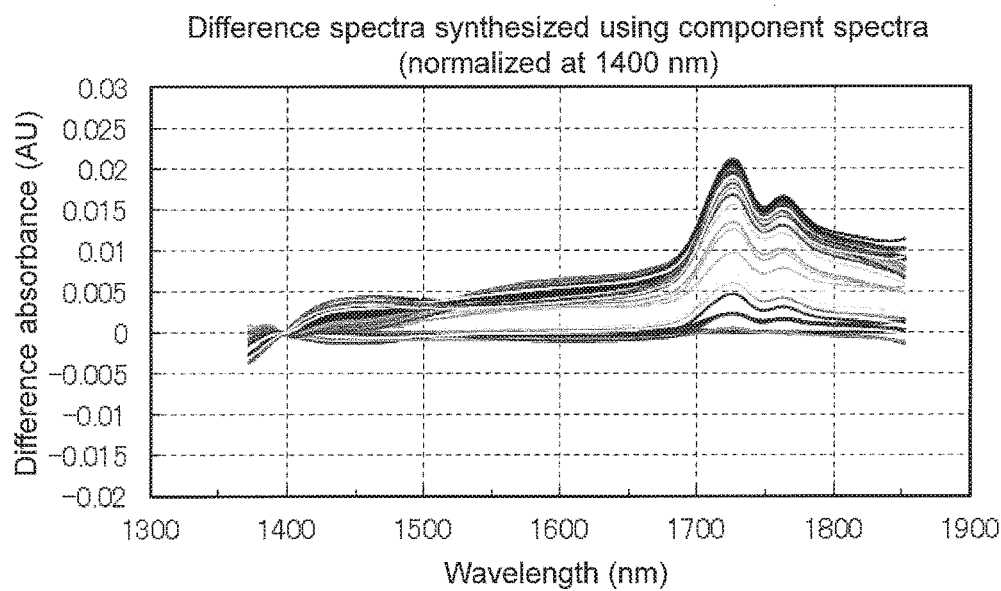
FIG. 19 is a diagram in which a change over time in the synthesized difference spectrum is plotted.

FIG. 19 is a diagram illustrating the change over time in a difference spectrum synthesized using the respective component spectra and the changes in the concentrations of the respective components calculated in each difference spectrum obtained every 5 minutes. The difference spectra shown in FIG. 19 are normalized at 1400 nm. When the graph of the change over time in the actually measured difference spectra shown in FIG. 16 and the graph of the change over time in the synthesized difference spectra shown in FIG. 19 are compared, the shapes of the graphs match well each other, and thus it can be seen that favorable synthesis of spectra can be performed.

Figure 20:
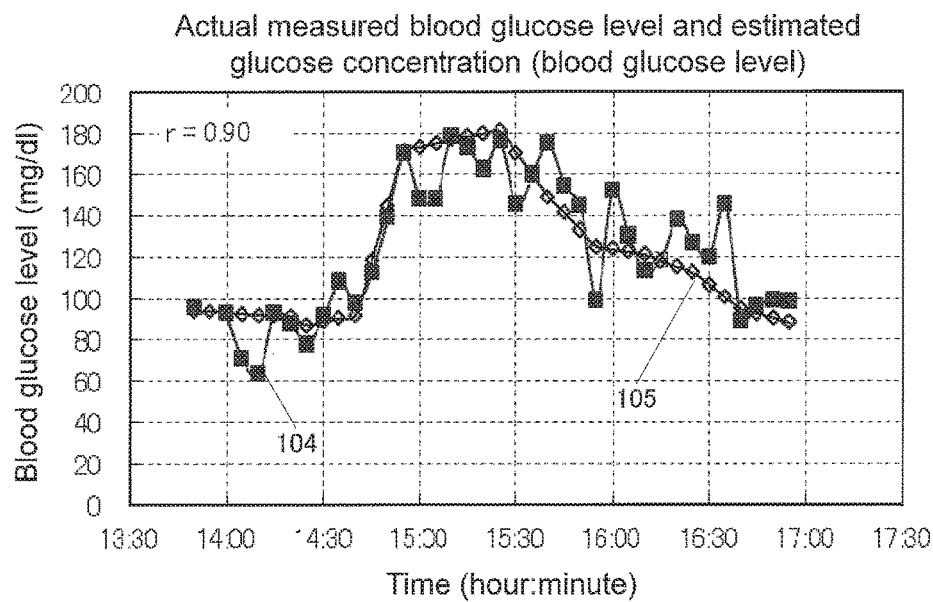
FIG. 20 is a diagram illustrating a change over time in an actual measured blood glucose level and a change over time in an estimated blood glucose level.

FIG. 20 shows a graph obtained by converting the obtained concentration index into the change in the blood glucose level and determining a constant term (V0) such that the blood glucose level at the start of the measurement matches the actual measured blood glucose level. As shown in FIG. 20, the correlation coefficient between the estimated blood glucose level 104 obtained by synthesizing the difference spectra and the actual measured blood glucose level 105 was 0.90.

In this embodiment, a conversion factor ($\alpha$) for converting a concentration index into a glucose concentration was 0.00005 (mg/dL)−1. The actual measured blood glucose level (V0) at the start of the measurement was 98 mg/dL.

As shown in FIG. 20, the change in the glucose concentration measured using the glucose concentration measurement device of this embodiment is highly correlated with the change in the actual measured blood glucose level obtained by actually measuring collected blood. Therefore, by merely collecting blood when a reference spectrum is measured, the change in the glucose concentration can be noninvasively measured in further measurements.

When the baseline in addition to water, glucose, and fat is a factor in the change in the difference spectrum, it is conceivable that the change in the baseline is treated as a factor for the synthesis of the difference spectrum in the same manner as the other biological components, and a determinant with four rows and four columns obtained by adding the baseline to the determinant with three rows and three columns produced using the biological component spectra of water, glucose, and fat in the embodiment 1 is used. However, with such a method, the shape of the spectrum of the glucose component is similar to the shape of the change in the baseline, thus becoming a large error factor. Therefore, by producing an imaginary spectrum using the baseline variation and the change in the fat spectrum, which are generated with the same mechanism, to synthesize a difference spectrum, the glucose component and the change in the baseline can be reliably separated, thus making it possible to improve the estimation accuracy.

In this embodiment, there is no limitation to the case where the change in the baseline is small as in Example 1, and a glucose concentration can be estimated accurately.

Embodiment 3

Hereinafter, a glucose concentration measurement device and a method for quantifying a glucose concentration of Embodiment 3 according to the present invention will be described.

3-1. Configuration of Glucose Concentration Measurement Device

The first imaginary spectrum producing unit 204 of a glucose concentration measurement device of this Embodiment 3 performs the smoothing processing using a moving average method instead of the integration average method, which is a smoothing processing method used in the Embodiment 2.

The glucose concentration measurement device and the measurement method according to the Embodiment 3 will be described in detail by way of Example 3.

3-2. Example 3

In this experiment, in the same manner as in Example 1, a glucose load was provided orally to a healthy subject, and the change in the blood glucose level (change in the glucose concentration in a biological tissue) was quantified. A blood glucose level was estimated according to the procedure shown in the flowchart as shown in FIG. 14 in the same manner as in Example 2.

Figure 21:
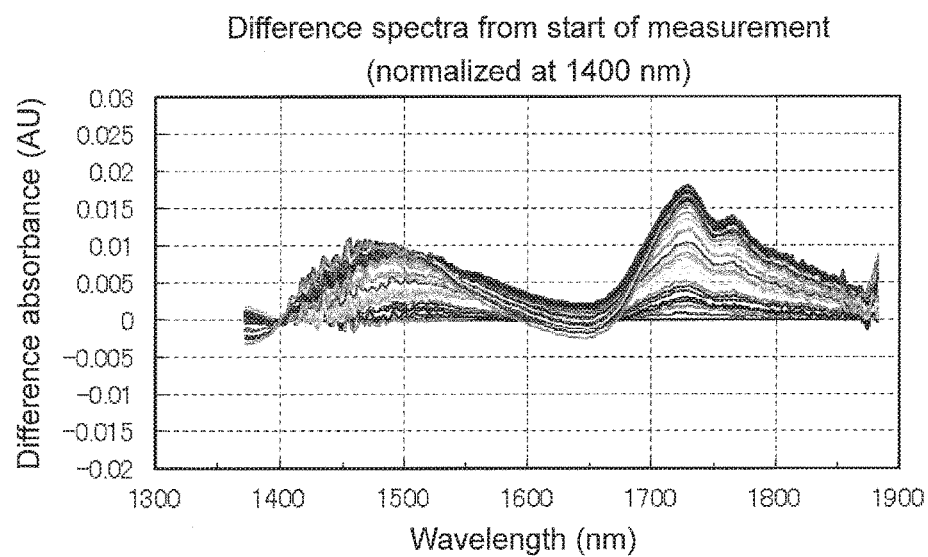
FIG. 21 is a diagram in which a change over time in the measured difference spectrum is plotted.

FIG. 21 is a diagram illustrating the change over time in a difference spectrum obtained by using the spectrum of the skin tissue at the start of the measurement as a reference to determine the difference from each of the measurement spectra. The difference spectra shown in FIG. 21 are normalized based on the absorbances at 1400 nm as described above. An increase in a baseline that is not as great as that in the Example 2 is observed at 1650 nm in the difference spectra.

In order to calculate the change over time in the glucose concentration in the skin tissue, the difference spectra shown in FIG. 21 were synthesized using the respective component spectra of the water 101 and the glucose component 102 shown in FIG. 6 and the imaginary spectrum produced in each spectral measurement.

As shown in FIG. 15, when the fat component 103 and the change in the baseline are added together, the imaginary spectrum can be calculated by adding together the amounts corresponding to the change in the baseline by Δs that is a change in the absorbance at 1650 nm, which represents the characteristic of the baseline of the difference spectrum 111, and the change in the fat spectrum by Δf that is a change in the difference between absorbances at 1650 nm and 1727 nm, which are the specific absorption wavelengths of the fat component, in the same manner as in the Embodiment 2.

In this embodiment, Δs, which is a change in an absorbance at 1650 nm in each of the difference spectra, and Δf, which is a change in the difference between absorbances at 1727 nm and 1650 nm, used values obtained by reducing the changes with the smoothing processing using not the integration average method but the moving average method. As the moving average, the average value of the measurement spectra at 25 points in total including 12 previous points and 12 subsequent points measured for about 2 hours was used. The reason why the moving average for 2 hours was used is that this period of time is sufficiently longer than the reaction time with respect to a glucose load in a healthy person.

Figure 22:
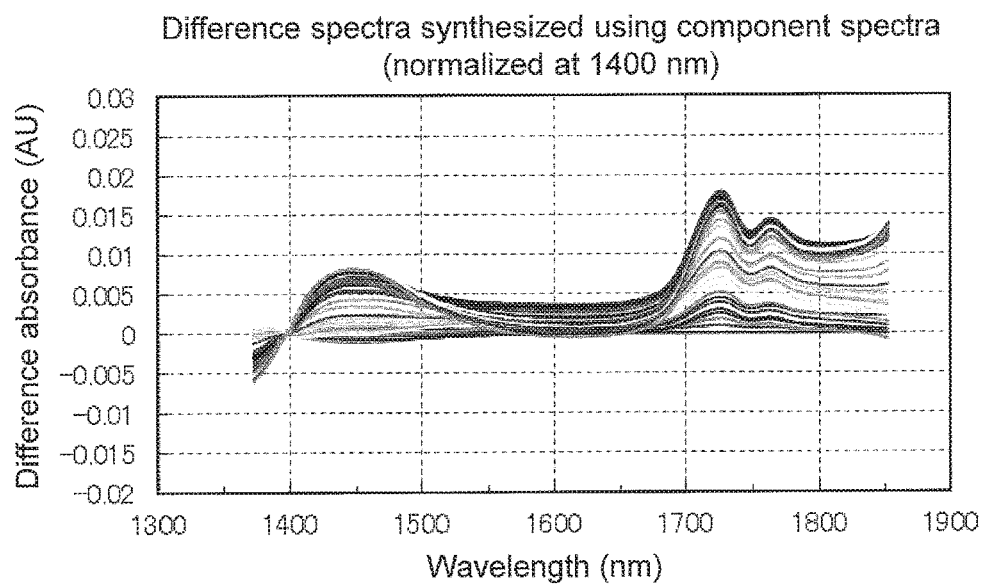
FIG. 22 is a diagram in which a change over time in the synthesized difference spectrum is plotted.

FIG. 22 is a diagram illustrating the change over time in a difference spectrum synthesized using the respective component spectra and the changes in the concentrations of the respective components calculated in each difference spectrum obtained every 5 minutes. The difference spectra shown in FIG. 22 are normalized at 1400 nm. When the shape of the actually measured difference spectra shown in FIG. 21 and the shape of the synthesized difference spectra shown in FIG. 22 are compared, the shapes match well each other, and thus it can be seen that favorable synthesis of spectra can be performed.

Figure 23:
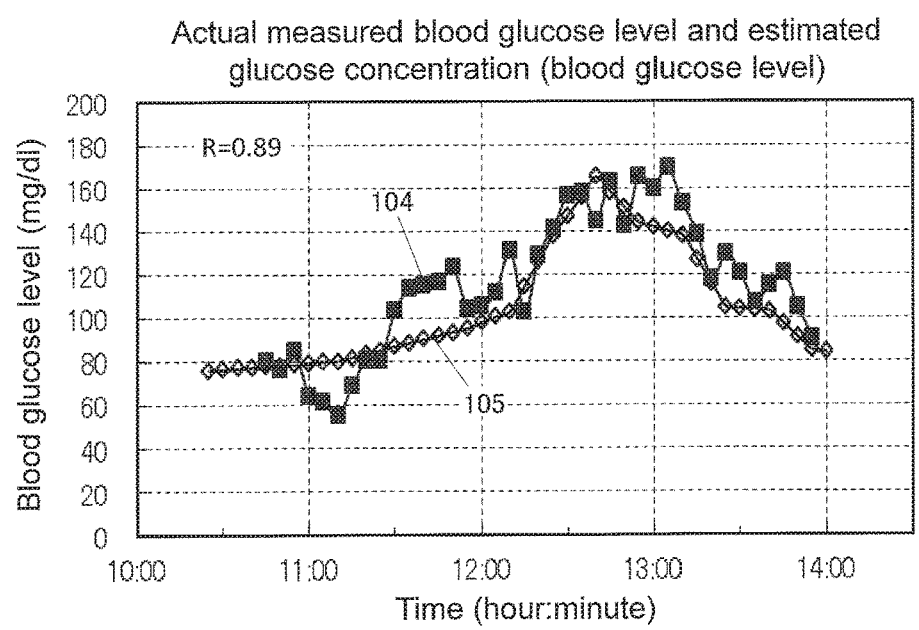
FIG. 23 is a diagram illustrating a change over time in an actual measured blood glucose level and a change over time in an estimated blood glucose level.

FIG. 23 shows a graph obtained by converting the obtained concentration index into the change in the blood glucose level and determining a constant term such that the blood glucose level at the start of the measurement matches the actual measured blood glucose level. As shown in FIG. 23, the correlation coefficient between the estimated blood glucose level 104 obtained by synthesizing the difference spectra and the actual measured blood glucose level 105 was 0.89.

In this embodiment, a conversion factor ($\alpha$) for converting a concentration index into a glucose concentration was 0.00005 (mg/dL)−1. The actual measured blood glucose level (V0) at the start of the measurement was 80 mg/dL.

Accordingly, even when the moving average method is used as the smoothing processing in the glucose concentration measurement device of this Embodiment 3, the change in the glucose concentration measured using the glucose concentration measurement device of this Embodiment 3 is highly correlated with the change in the actual measured blood glucose level obtained by actually measuring collected blood.

Embodiment 4

Hereinafter, a glucose concentration measurement device of an Embodiment 4 according to the present invention will be described.

Although the methods of coping with the so-called change in the baseline are described in the Embodiment 2, 3, the CLS method has a disadvantage in which the quantification accuracy decreases due to unexpected disturbance factors. It can be said that the occurrence of unexpected disturbance is in a sense inevitable in spectral measurement of a living organism, and it is important to realize measures against the disturbances in order to improve the accuracy. This embodiment relates to a method of suppressing the decrease in the quantification accuracy caused by the occurrence of unexpected unknown disturbance.

With this embodiment, it is possible to more accurately estimate a blood glucose level by not identifying unexpected unknown disturbance factors but finding the amount of errors given to the estimated value of the blood glucose level by the unexpected disturbance factors and subtracting the amount of errors from the estimated value.

4-1. Glucose Concentration Measurement Device

The arithmetic device 17 of the glucose concentration measurement device of this Embodiment 4 has a configuration different from those of the arithmetic devices of the Embodiments 1 to 3, and therefore, the differences will be mainly described.

Figure 24:
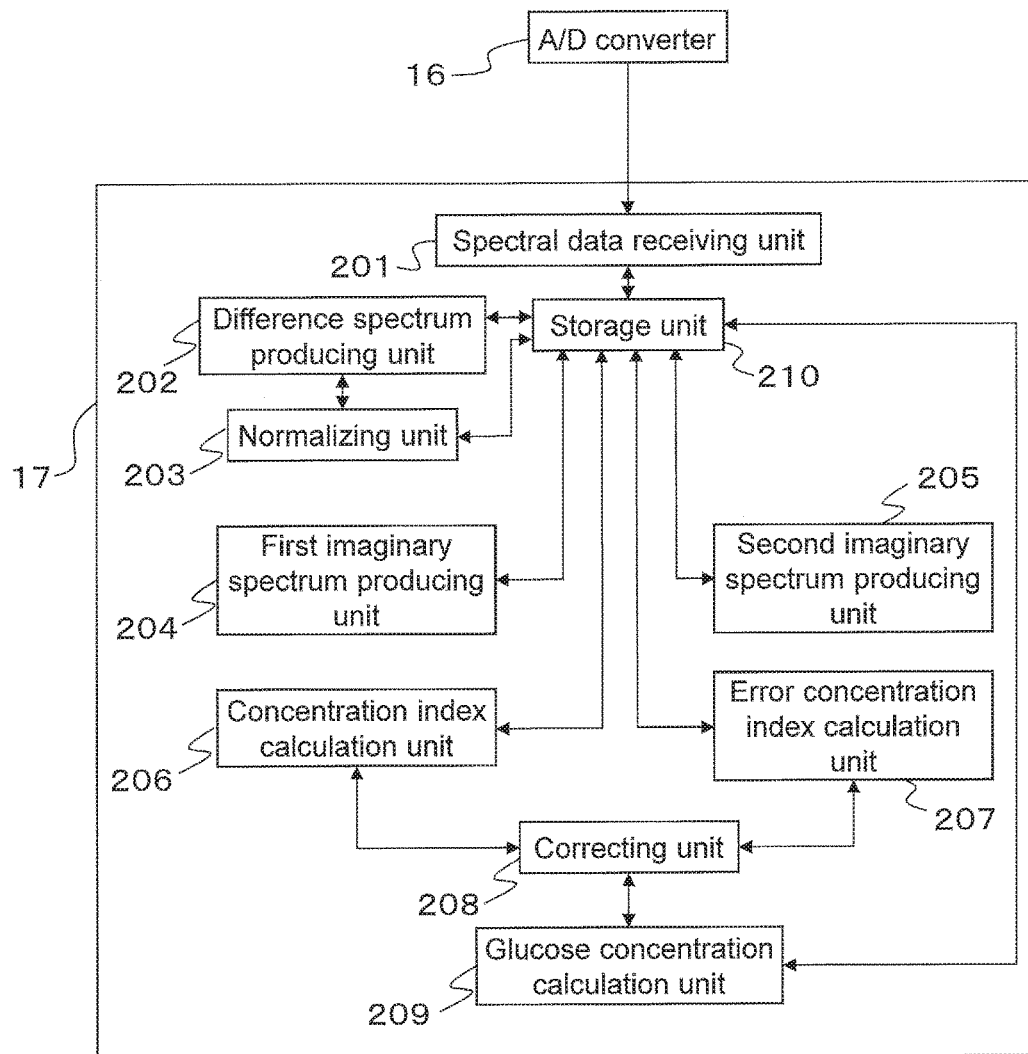
FIG. 24 is a block diagram illustrating a configuration of an arithmetic unit of a glucose concentration measurement device of Embodiment 4.

FIG. 24 is a diagram illustrating a configuration of the arithmetic device 17 (see FIG. 1) of the glucose concentration measurement device of this embodiment.

As shown in FIG. 24, the arithmetic device 17 of the glucose concentration measurement device of this embodiment includes the spectral data receiving unit 201, the difference spectrum producing unit 202, the normalizing unit 203, the first imaginary spectrum producing unit 204, a second imaginary spectrum producing unit 205, the concentration index calculation unit 206, an error concentration index calculation unit 207, a correcting unit 208, the glucose concentration calculation unit 209, and the storage unit 210.

The spectral data receiving unit 201 receives spectral data that has undergone digital conversion by the A/D converter 16 and sends the data to the storage unit 210.

The difference spectrum producing unit 202 computes the difference between a spectrum that is received by the spectral data receiving unit 201 at the time of the measurement of a glucose concentration and a reference spectrum that is received therebefore and stored in the storage unit 210, and produces a difference spectrum.

The normalizing unit 203 normalizes the difference spectrum by subtracting an absorbance of the difference spectrum at 1400 nm from the absorbances of the difference spectrum.

The first imaginary spectrum producing unit 204 includes an averaging means, the averaging means performs smoothing processing on the normalized difference spectrum in the same manner as in the second embodiment or the third embodiment, and a first imaginary spectrum is produced using the change in the baseline in that spectrum and the change in the spectrum of the fat component.

The second imaginary spectrum producing unit 205 produces a second imaginary spectrum using, in a normalized difference spectrum, the change in the baseline and the change in the spectrum of the fat component, which have not undergone the smoothing processing.

The concentration index calculation unit 206 uses the first imaginary spectrum, and spectral data of a water component and spectral data of a glucose component stored in the storage unit 210 to synthesize the difference spectrum obtained by subtracting the reference spectrum from the spectrum obtained at the time of the measurement of a glucose concentration and normalizing the resulting spectrum, and calculates a concentration index CG.

The error concentration index calculation unit 207 uses the second imaginary spectrum, the spectral data of the water component, and the spectral data of the glucose component to synthesize the difference spectrum obtained by subtracting the reference spectrum from the spectrum obtained at the time of the measurement of a glucose concentration and normalizing the resulting spectrum, and calculates an error concentration index CError.

The correcting unit 208 corrects the concentration index CG by subtracting the error concentration index CError from the concentration index CG.

The glucose concentration calculation unit 209 calculates a glucose concentration by matching the glucose concentration at the time of the measurement of a reference spectrum with the actual measured blood glucose level at that time, converting the corrected concentration index CG into the change in the glucose concentration, and adding the converted change in the glucose concentration to the glucose concentration at the time of the measurement of a reference spectrum.

The conversion factor to be used to convert a concentration index CG value into a change in the glucose concentration, the spectral data at the time of the measurement of a glucose concentration, the reference spectral data, the difference spectrum, the difference spectrum normalized at 1400 nm, the first imaginary spectrum data, the second imaginary spectrum data, the spectral data of the water component, the spectral data of the glucose component, and the like are stored in the storage unit 210.

4-2. Method for Quantifying Blood Glucose Level

Figure 25:
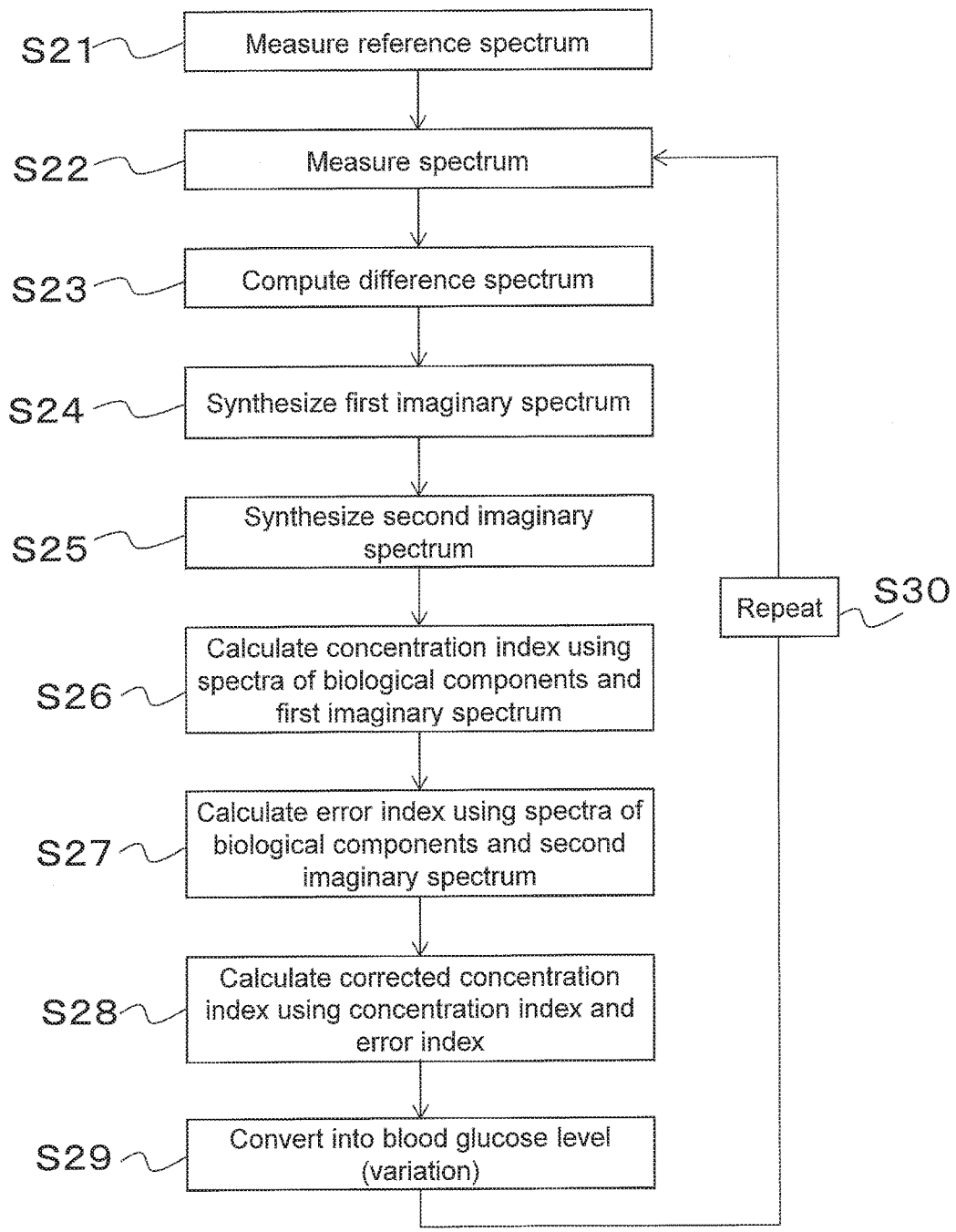
FIG. 25 is a flowchart illustrating a measurement procedure in the Embodiment 4.

According to the procedure shown in the flowchart as shown in FIG. 25, a blood glucose level is estimated in the same manner as in the Embodiment 2, except that an error given to the estimated blood glucose value by the unexpected disturbance factors is calculated.

The measurement is started after a lapse of 45 minutes from which the measurement probe 9 was attached.

In step S21 (indicated as S21 in FIG. 25), a measurement spectrum at the start of the measurement is set to be a reference spectrum.

In step S22 (indicated as S22 in FIG. 25), a spectrum is measured.

In step S23 (indicated as S23 in FIG. 25), the difference spectrum producing unit 202 determines a differential spectrum between the reference spectrum and each measurement spectrum and calculates difference spectra. Here, the normalizing unit 203 normalizes the difference spectra based on absorbances at 1400 nm (an example of a normalizing step), and the normalized difference spectra are stored in the storage unit 210.

In step S24 (indicated as S24 in FIG. 25), the first imaginary spectrum producing unit 204 produces a first imaginary spectrum using in the normalized difference spectrum, the change in the baseline and the change in the spectrum of the fat component, which have undergone the smoothing processing. Step S24 corresponds to an example of a first imaginary spectrum producing step.

In step S25 (indicated as S25 in FIG. 25), the second imaginary spectrum producing unit 205 produces a second imaginary spectrum using, in the normalized difference spectrum, the change in the baseline and the change in the spectrum of the fat component, which have not undergone the smoothing processing. Step S25 corresponds to an example of a second imaginary spectrum producing step.

In step S26 (indicated as S26 in FIG. 25), the concentration index calculation unit 206 synthesizes the obtained normalized difference spectrum using the spectra of the biological components and the first imaginary spectrum and calculates the concentration index CG of the glucose component. Step S26 is an example of a concentration index calculation step. The spectra of the biological components (the spectrum of the water component and the spectrum of the fat component) and the first imaginary spectrum are normalized based on the absorbances at 1400 nm. FIG. 26(*a*) is a diagram illustrating a determinant (three rows and three columns) used to calculate the concentration index CG. Specifically, as shown in FIG. 26(*a*), a determinant with three rows and three columns is produced using the first imaginary spectrum, and then an inverse matrix is used to calculate the glucose concentration index CG. In FIG. 26(*a*), I1 represents the first imaginary spectrum.

In step S27 (indicated as S27 in FIG. 25), the error concentration index calculation unit 207 synthesizes the obtained normalized difference spectrum using the spectra of the biological components and the second imaginary spectrum and calculates the error concentration index CError of the glucose component. Step S27 is an example of an error concentration index calculation step. The spectra of the biological components (the spectrum of the water component and the spectrum of the fat component) and the second imaginary spectrum are normalized based on the absorbances at 1400 nm.

In step S28 (indicated as S28 in FIG. 25), the correcting unit 208 subtracts the error concentration index CError of the glucose component from the concentration index CG of the glucose component obtained by synthesizing the difference spectrum and provides a concentration index CG' of the glucose component obtained by correcting the error. Step S28 is an example of a correcting step.

In step S29 (indicated as S29 in FIG. 25), the glucose concentration calculation unit 209 converts the above-mentioned concentration index CG' of the glucose component obtained by correcting the error in step S28 into a blood glucose level. Step S29 is an example of a glucose concentration calculation. That is, a glucose concentration Vt is calculated based on an equation $Vt=V0+\alpha \times CG'$.

In step S30 (indicated as S30 in FIG. 25), the operations after step S22 are repeated every 5 minutes until the measurement is finished.

The error concentration index CError described in step S27 in the flowchart shown in FIG. 25 can be obtained by producing the second imaginary spectrum using the change in the baseline and the change in the spectrum of the fat component, which have not undergone the smoothing processing, in step S25, and synthesizing the difference spectrum with the same method as the method of calculating the concentration index of the glucose component.

FIG. 26(b) is a diagram illustrating a determinant (three rows and three columns) to be used to calculate the error index CError.

Specifically, as shown in FIG. 26(b), a determinant with three rows and three columns is produced using the second imaginary spectrum, and then an inverse matrix is used to calculate the glucose error concentration index CError. In FIG. 26(b), I2 represents the second imaginary spectrum.

It is conceivable that the obtained error concentration index CError is an error included in the glucose concentration index CG obtained from the first imaginary spectrum. The reason for this will be described below.

Error Concentration Index

When the fat spectrum and the change in the baseline are added together as described in step S25 in the flowchart shown in FIG. 25, the second imaginary spectrum 2 (I2(Δs, Δf)) is calculated by adding together the change in the baseline by Δs that is a change in the absorbance at 1650 nm, which represents the characteristic of the baseline of the difference spectrum, and the change in the fat spectrum by Δf that is a change in the difference between absorbances at 1650 nm and 1727 nm, which are the specific absorption wavelengths of the fat component, in the same manner as in the second embodiment as shown in FIG. 15.

Here, since the smoothing processing is not performed, the change in the glucose concentration is superposed onto the change in the absorbance at 1650 nm, and thus a change Δg caused by the change in glucose and a change Δb in a baseline adds up to Δs. As described above, the change in the baseline and the change in the glucose component have a similar shape, and therefore, if the difference spectrum is synthesized without performing the smoothing processing, the absorbance in an amount substantially corresponding to the glucose component will be included in the change in the baseline. Therefore, although the same computation as the computation for estimating the glucose concentration index is performed, the calculated index (CError) is a value from which almost all of the glucose component is removed.

To understand the description above, assuming that the change in the baseline has the completely same spectral shape as the shape of the glucose spectrum, Δs obtained from raw data is a value obtained by adding together the baseline and the change in the glucose concentration. Therefore, in the computation of the raw data, a determinant is calculated using the second imaginary spectrum in which the glucose is superposed onto the change in the baseline as a disturbance factor. However, when the target glucose concentration index is computed, the second imaginary spectrum is removed as a contribution given to the change in the measurement spectrum (difference spectrum), and the change in the glucose component is removed simultaneously. That is, if the change in the measurement spectrum (difference spectrum) can be entirely explained using three items: water, glucose, and the second imaginary spectrum, the computed glucose concentration index will be zero.

Generally, the estimation of a minor component such as glucose is significantly affected by the error factors other than the main disturbance factors such as water, fat, and the baseline, and therefore, the glucose concentration index is not zero, and a certain value corresponding to the influence of the error factors is calculated. Such a value is considered as an error caused by factors other than main disturbance and set to be the CError as mentioned above.

Of course, in practice, the baseline spectrum dose not completely match the glucose spectrum as assumed above, and therefore, an error caused by the mismatch will occur.

That is, as a result of the two spectral syntheses performed using the same difference spectrum, when the smoothing processing is performed, the glucose concentration (CG) is estimated, and when the smoothing processing is not performed, an error (CError) included in the estimated index is estimated. Therefore, the error can be corrected by subtracting CError from CG.

As described above, the difference spectrum obtained by subtracting the reference spectrum from the measurement spectrum is normalized at 1400 nm and then undergoes the smoothing processing, and the first imaginary spectrum is obtained using, in the spectrum, the change in the baseline and the change in the spectrum of the fat component, which have undergone the smoothing processing. In this first imaginary spectrum, the superposition of the change in the glucose concentration on the change in the baseline and the change in the spectrum of the fat component is reduced as much as possible by performing the smoothing processing. The concentration index CG of the glucose component is obtained by synthesizing a spectrum using this first imaginary spectrum, and the component spectra of water and glucose.

On the other hand, with regard to the second imaginary spectrum, the difference spectrum obtained by subtracting the reference spectrum from the measurement spectrum is normalized at 1400 nm and then does not undergo the smoothing processing, and the second imaginary spectrum is obtained using, in the spectrum, the change in the baseline and the change in the spectrum of the fat component, which have not undergone the smoothing processing. The change in the glucose concentration is superposed onto the change in the baseline and the change in the spectrum of the fat component. When a spectrum is synthesized using this second imaginary spectrum, and the component spectra of water and glucose, CI2 on the second imaginary spectrum side includes the concentration index of the glucose component, and the error concentration index CError including no glucose component represents the error remaining in the above-mentioned concentration index CG of the glucose component.

Next, the glucose concentration measurement device and the measurement method according to this Embodiment 4 will be described in detail by way of experimental examples in Example 4 and Example 5.

4-3. Example 4

This Example 4 is an experimental example in which a glucose load was provided orally to a healthy subject and the change in the blood glucose level was estimated in the same manner as in Example 1 and Example 2. The blood glucose level was estimated according to the flowchart shown in FIG. 25.

FIG. 27 shows the relationship between the value obtained by converting the glucose concentration index (CG) in the case where the smoothing processing is performed into a concentration with the integration average method on each of the difference spectra obtained every 5 minutes, and the value obtained by converting the error (CError) included in the index in the case where raw data that has not undergone the smoothing processing is used into a concentration.

FIG. 27(a) is a diagram illustrating a graph of the estimated blood glucose level 104 obtained by converting the glucose concentration index (CG) in the case where the smoothing processing is performed into a concentration. FIG. 27(b) is a diagram illustrating a graph of the estimation error 114 obtained by converting the error (CError) included in the index in the case where raw data that has not undergone the smoothing processing is used into a concentration.

The graph shown in FIG. 27(a) illustrates the change over time in the estimated blood glucose level 104 obtained by converting the glucose concentration estimation index (CG) in the case where the smoothing processing is performed into a blood glucose level with a conversion factor of 0.00007 (mg/dL)−1, and when compared with the actual measured blood glucose level 105, it can be seen that the estimated blood glucose level increases even in a period of time before 13:00 in which the blood glucose level is stable. This suggests that unknown errors have occurred that cannot be entirely removed with the method shown in the Embodiment 2.

After providing the glucose load at 13:00, it seems that the variation in the blood glucose level caused by the glucose load has been superposed, but it is not clear.

On the other hand, the graph shown in FIG. 27(b) illustrates the change over time in the estimation error 114 obtained by converting the error (CError) included in the index in the case where raw data that has not undergone the smoothing processing is used into a blood glucose level with a conversion factor of 0.00007 (mg/dL)−1, and when compared with the actual measured blood glucose level 105, it can be seen that the estimated blood glucose level increases even in a period of time before 13:00 in which the blood glucose level is stable, as in the graph on the upper side. After providing the glucose load at 13:00, a change corresponding to the change in the blood glucose level caused by the glucose load is significantly reduced.

Figure 28:
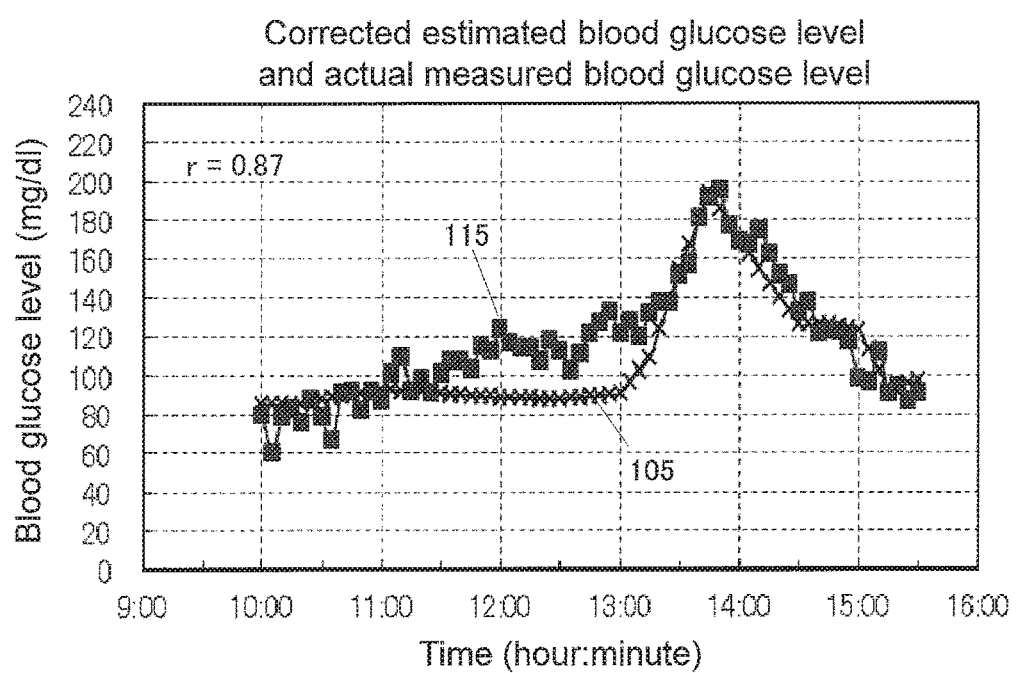
FIG. 28 is a diagram illustrating a change over time in an actual measured blood glucose level and a change over time in a corrected estimated blood glucose level.

FIG. 28 shows the relationship between the actual measured blood glucose level 105 and an estimated blood glucose level 115 in which an error is corrected by calculating the difference between the glucose concentration index (CG) and the error (CError), converting the difference into a blood glucose level with a conversion factor of 0.000035 (mg/dL)−1 (α), and matching the initial blood glucose level with 95 mg/dl (V0), which is the actual measured blood glucose level at the start of the measurement. The correlation coefficient between the actual measured blood glucose level and the estimated blood glucose level was 0.87.

It can be considered that the reason why the conversion factor of this embodiment (0.000035 (mg/dL)−1) is slightly smaller than the conversion factor in Example 1 and Example 2 (0.00005 (mg/dL)−1) is that the glucose component also remains in the error (CError). It is inferred that the reason for this is that the shape of the glucose spectrum and the shape of the baseline variation are not completely the same but slightly different.

With the method of this embodiment, it is possible to correct the error caused by unknown disturbance components, and therefore, it is possible to accurately quantify the glucose concentration even in the case where the number of components in the measured spectrum is different from the number of components in the component spectrum to be used in the synthesis, resulting in the contamination of unknown disturbances, which is a disadvantage of the spectral synthesis method.

As described above, it is possible to simply and accurately quantify the concentrations of the components in a living organism, particularly the glucose concentration, by synthesizing the difference spectrum and correcting the amount of the errors.

4-4. Example 5

In this Example 5, the estimation of the glucose concentration was performed on a healthy subject according to the procedure shown in the flowchart as shown in FIG. 25 in the same manner as in Example 4. Example 5 differs from Example 4 of this embodiment in that a second glucose load was provided at the time when the glucose concentration returned to around the initial value after a first glucose load was provided.

Figure 29:
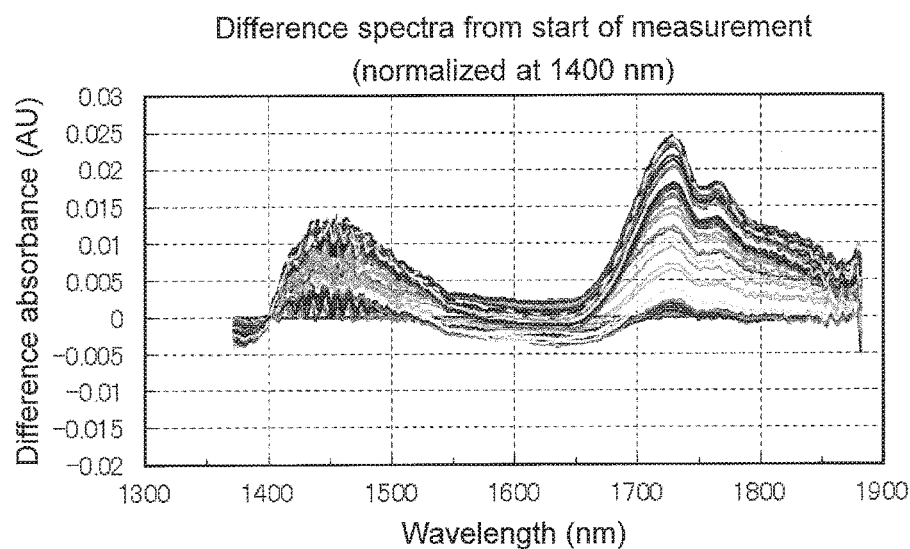
FIG. 29 is a diagram in which a change over time in the measured difference spectrum is plotted.

FIG. 29 is a diagram illustrating the change over time in the difference spectrum obtained by using the spectrum of the skin tissue at the start of the measurement as a reference to determine the difference from each of the measurement spectra. The difference spectra shown in FIG. 29 are normalized based on the absorbances at 1400 nm as described above.

Figure 30:
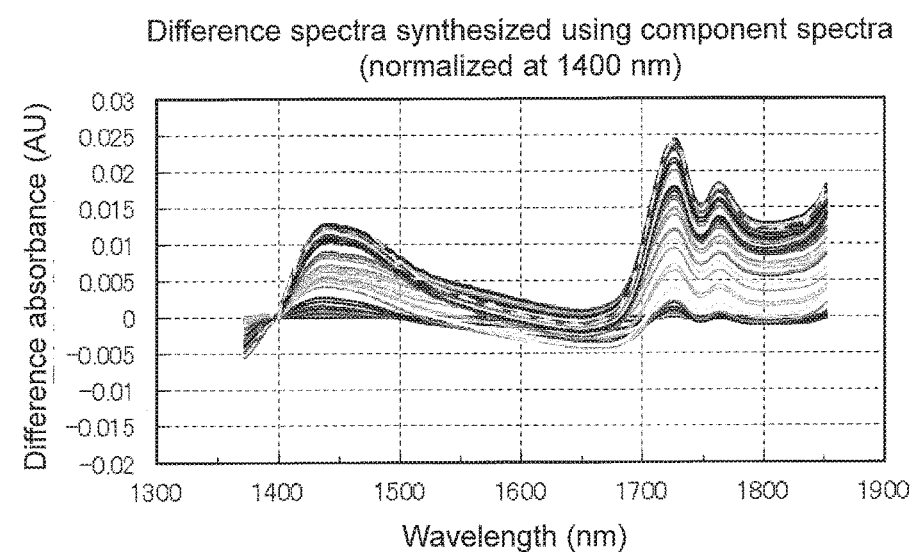
FIG. 30 is a diagram in which a change over time in the synthesized difference spectrum is plotted.

In order to calculate the change over time in the glucose concentration in the skin tissue, the difference spectra shown in FIG. 29 were synthesized using the respective component spectra of the water 101 and the glucose component 102 shown in FIG. 6 and the first imaginary spectrum and the second imaginary spectrum produced in each spectral measurement. FIG. 30 is a diagram illustrating the change over time in the synthesized difference spectrum. In this embodiment, the smoothing was performed with the integration average method.

When FIG. 29 and FIG. 30 are compared, the spectral shapes match well each other, and thus it can be seen that favorable synthesis of spectra can be performed.

FIG. 31 shows the relationship between the actual measured blood glucose level 105 and the estimated blood glucose level 115 obtained by determining the difference between the glucose concentration index (CG) in the case where the smoothing processing is performed with the integration average method on each difference spectrum obtained every 5 minutes and the error (CError) obtained from raw data that has not undergone the smoothing processing and correcting the error. A conversion factor (α) for converting a concentration index into a glucose concentration was 0.000035 (mg/dL)−1.

The actual measured blood glucose level (V0) at the start of the measurement was 95 mg/dL, and the initial blood glucose level was matched with this value.

The correlation coefficient between the actual measured blood glucose level and the estimated blood glucose level was 0.78.

It can be confirmed that it is possible to favorably estimate a blood glucose level even in a complicated change in the blood glucose level due to the glucose load being applied twice, as in this embodiment.

Embodiment 5

Hereinafter, a glucose concentration measurement device and a method for quantifying a glucose concentration of Embodiment 5 according to the present invention will be described.

The method of suppressing the decrease in the quantification accuracy caused by the occurrence of unexpected unknown disturbances is described in Example 4 and Example 5 of the Embodiment 4 mentioned above. In this Embodiment 5, the difference spectrum was synthesized using the water 101, the glucose component 102, the fat component 103, and a protein (collagen) component 116 shown in FIG. 6 as well as the baseline. The synthesis was performed in the same manner as in Embodiment 4, except that the protein (collagen) component 116 was added. An absorbance at a characteristic wavelength selected from the wavelength range of 1510±30 nm was used as the characteristic absorption wavelength of the spectrum of the protein component to be used to synthesize the difference spectrum.

5-1. Configuration of Glucose Concentration Measurement Device

The arithmetic device 17 (see FIG. 1) of the glucose concentration measurement device of this embodiment has the same configuration as that of Embodiment 4, and includes the spectral data receiving unit 201, the difference spectrum producing unit 202, the normalizing unit 203, the first imaginary spectrum producing unit 204, the second imaginary spectrum producing unit 205, the concentration index calculation unit 206, the error concentration index calculation unit 207, the correcting unit 208, the glucose concentration calculation unit 209, and the storage unit 210.

The spectral data receiving unit 201 receives spectral data that has undergone digital conversion by the A/D converter 16 and sends the data to the storage unit 210.

The difference spectrum producing unit 202 computes the difference between a spectrum that is received by the spectral data receiving unit 201 at the time of the measurement of a glucose concentration and a reference spectrum that is received therebefore and stored in the storage unit 210, and produces a difference spectrum.

The normalizing unit 203 normalizes the difference spectrum by subtracting an absorbance of the difference spectrum at 1400 nm from the absorbances of the difference spectrum.

The first imaginary spectrum producing unit 204 includes an averaging means, the averaging means performs smoothing processing on the normalized difference spectrum, and a first imaginary spectrum is produced using, in that spectrum, the change in the baseline and the change in the spectrum of the fat component.

The second imaginary spectrum producing unit 205 produces a second imaginary spectrum using, in a normalized difference spectrum, the change in the baseline and the change in the spectrum of the fat component, which have not undergone the smoothing processing.

The concentration index calculation unit 206 uses the first imaginary spectrum, and spectral data of a water component, spectral data of a protein (collagen) component, and spectral data of a glucose component stored in the storage unit 210 to synthesize, using a determinant with four rows and four columns as shown in FIG. 32, the difference spectrum obtained by subtracting the reference spectrum from the spectrum obtained at the time of the measurement of a glucose concentration and normalizing the resulting spectrum, and calculates a concentration index CG. The characteristic wavelength of the spectrum of the protein component was 1510 nm. I1 shown in FIG. 32 represents the first imaginary spectrum. In addition, in FIG. 32, P represents the spectrum of the protein component, W represents the spectrum of the water component, and G represents the spectrum of the glucose component.

The error concentration index calculation unit 207 uses the second imaginary spectrum, the spectral data of the water component, the spectral data of the protein (collagen) component, and the spectral data of the glucose component to synthesize, using the determinant with four rows and four columns as shown in FIG. 33, the difference spectrum obtained by subtracting the reference spectrum from the spectrum obtained at the time of the measurement of a glucose concentration is measured and normalizing the resulting spectrum, and calculates an error concentration index CError. I2 shown in FIG. 33 represents the second imaginary spectrum.

The correcting unit 208 corrects the concentration index CG by subtracting the error concentration index CError from the concentration index CG.

The glucose concentration calculation unit 209 calculates a glucose concentration by matching the glucose concentration at the time of the measurement of a reference spectrum with the actual measured blood glucose level at that time, converting the corrected concentration index CG into the change in the glucose concentration, and adding the converted change in the glucose concentration to the glucose concentration at the time of the measurement of a reference spectrum.

The conversion factor to be used to convert a concentration index CG value into a change in the glucose concentration, the spectral data at the time of the measurement of a glucose concentration, the reference spectral data, the difference spectrum, the difference spectrum normalized at 1400 nm, the first imaginary spectrum data, the second imaginary spectrum data, the spectral data of the water component, the spectral data of the protein (collagen) component, the spectral data of the glucose component, and the like are stored in the storage unit 210.

5-2. Method for Quantifying Blood Glucose Level

Next, a method for quantifying a glucose concentration according to this Embodiment 5 will be described.

A blood glucose level is estimated according to the procedure shown in the flowchart as shown in FIG. 25.

The measurement is started after a lapse of 45 minutes, for example, from which the measurement probe 9 was attached.

In step S21 (indicated as S21 in FIG. 25), a measurement spectrum at the start of the measurement is set to be a reference spectrum.

In step S22 (indicated as S22 in FIG. 25), a spectrum is measured.

In step S23 (indicated as S23 in FIG. 25), the difference spectrum producing unit 202 determines a differential spectrum between the reference spectrum and each measurement spectrum and calculates difference spectra. Here, the normalizing unit 203 normalizes the difference spectra based on absorbances at 1400 nm (an example of a normalizing step), and the normalized difference spectra are stored in the storage unit 210.

In step S24 (indicated as S24 in FIG. 25), the first imaginary spectrum producing unit 204 produces a first imaginary spectrum using, in the normalized difference spectrum, the change in the baseline and the change in the spectrum of the fat component, which have undergone the smoothing processing. Step S24 corresponds to an example of a first imaginary spectrum producing step.

In step S25 (indicated as S25 in FIG. 25), the second imaginary spectrum producing unit 205 produces a second imaginary spectrum using, in the normalized difference spectrum, the change in the baseline and the change in the spectrum of the fat component, which have not undergone the smoothing processing. Step S25 corresponds to an example of a second imaginary spectrum producing step.

In step S26 (indicated as S26 in FIG. 25), the concentration index calculation unit 206 synthesizes the obtained normalized difference spectrum using the spectra of the biological components and the first imaginary spectrum and calculates the concentration index CG of the glucose component. Step S26 is an example of a concentration index calculation step. The spectra of the biological components (the spectrum of the water component, the spectrum of the fat component) and the first imaginary spectrum are normalized based on the absorbances at 1400 nm.

In step S27 (indicated as S27 in FIG. 25), the error concentration index calculation unit 207 synthesizes the obtained normalized difference spectrum using the spectra of the biological components and the second imaginary spectrum and calculates the error concentration index CError of the glucose component. Step S27 is an example of an error concentration index calculation step. The spectra of the biological components (the spectrum of the water component, the spectrum of the protein component, the spectrum of the fat component) and the first imaginary spectrum are normalized based on the absorbances at 1400 nm.

In step S28 (indicated as S28 in FIG. 25), the correcting unit 208 subtracts the error concentration index of the glucose component from the concentration index of the glucose component obtained by synthesizing the difference spectrum and provides a concentration index of the glucose component obtained by correcting the error. Step S28 is an example of a correcting step.

In step S29 (indicated as S29 in FIG. 25), the glucose concentration calculation unit 209 converts the above-mentioned concentration index of the glucose component obtained by correcting the difference in step S28 into a blood glucose level. Step S29 is an example of a glucose concentration calculation.

In step S30 (indicated as S30 in FIG. 25), the operations after step S22 are repeated every 5 minutes until the measurement is finished.

The error concentration index CError described in step S27 in the flowchart shown in FIG. 25 can be obtained by producing the second imaginary spectrum using the change in the baseline and the change in the spectrum of the fat component, which have not undergone the smoothing processing, in step S25, and synthesizing the difference spectrum with the same method as the method of calculating the concentration index of the glucose component.

As described above, the difference spectrum obtained by subtracting the reference spectrum from the measurement spectrum is normalized at 1400 nm and then undergoes the smoothing processing, and the first imaginary spectrum is obtained using, in the spectrum, the change in the baseline and the change in the spectrum of the fat component, which has undergone the smoothing processing. In this first imaginary spectrum, the superposition of the change in the glucose concentration onto the change in the baseline and the change in the spectrum of the fat component is reduced as much as possible by performing the smoothing processing. The concentration index CG of the glucose component is obtained by synthesizing a spectrum using this first imaginary spectrum, and the component spectra of water, glucose, and protein.

On the other hand, with regard to the second imaginary spectrum, the difference spectrum obtained by subtracting the reference spectrum from the measurement spectrum is normalized at 1400 nm and then does not undergo the smoothing processing, and the second imaginary spectrum is obtained using, in the spectrum, the change in the baseline and the change in the spectrum of the fat component, which have not undergone the smoothing processing. The change in the glucose concentration is superposed onto the change in the baseline and the change in the spectrum of the fat component. When a spectrum is synthesized using this second imaginary spectrum, and the component spectra of water, glucose, and protein, CI2 on the second imaginary spectrum side includes the concentration index of the glucose component, and the error concentration index CError including no glucose component represents the error remaining in the above-mentioned concentration index CG of the glucose component.

Next, the glucose concentration measurement device and the method for quantifying a glucose concentration according to this Embodiment 5 will be described in detail by way of Example 6, which is an experimental example.

5-3. Example 6

This Example 6 is an experimental example in which a glucose load was provided orally to a healthy subject and the change in the blood glucose level (change in the glucose concentration in a biological tissue) was estimated in the same manner as in Example 1 to Example 5. The blood glucose level was estimated according to the flowchart shown in FIG. 25.

Figure 34:
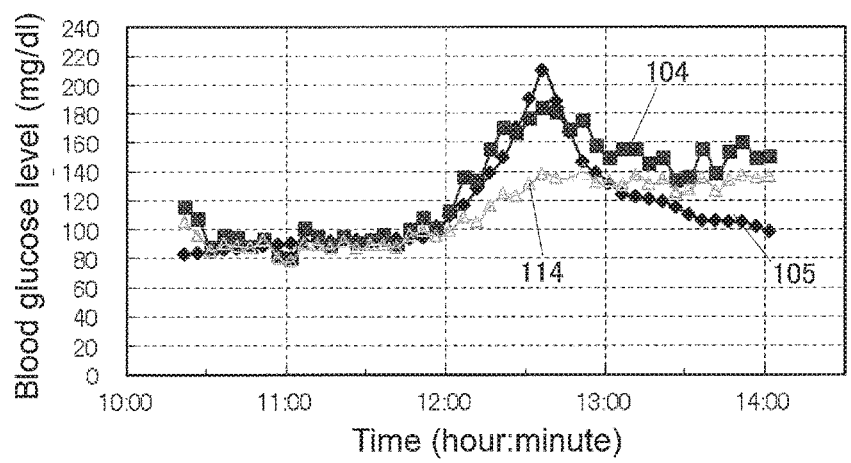
FIG. 34 is a diagram for comparing an estimated blood glucose level obtained by performing smoothing processing and an estimation error obtained without performing smoothing processing.

FIG. 34 shows the relationship between the value obtained by converting the glucose concentration index (CG) in the case where the smoothing processing is performed into a concentration with the integration average method for each of the difference spectra obtained every 5 minutes, and the value obtained by converting the error (CError) included in the index in the case where raw data that has not undergone the smoothing processing is used into a concentration.

FIG. 34 is a diagram illustrating a graph of the estimated blood glucose level 104 obtained by converting the glucose concentration index (CG) in the case where the smoothing processing is performed into a concentration, and a graph of the estimation error 114 obtained by converting the error (CError) included in the index in the case where raw data that has not undergone the smoothing processing is used into a concentration.

A conversion factor for converting the indices of 104 and 114 into a concentration was 0.00007 (mg/dL)−1. Also, the change over time in the actual measured blood glucose level 105 obtained by actually measuring collected blood is plotted in the graph for reference.

The graph 104 shown in FIG. 34 illustrates the change over time in the estimated blood glucose level obtained by converting the glucose concentration estimation index (CG) in the case where the smoothing processing is performed into the blood glucose level with a conversion factor of 0.00007 (mg/dL)−1, and when compared with the actual measured blood glucose level 105, it can be seen that the estimated blood glucose level continuously increases after 12:00. This suggests that unknown errors have occurred that cannot be entirely removed with the method shown in the Embodiment 2. After providing the glucose load at 12:00, it seems that the variation in the blood glucose level caused by the glucose load has been superposed, but it is not clear.

On the other hand, the graph 114 shown in FIG. 34 illustrates the change over time in the estimation error obtained by converting the error (CError) included in the index in the case where raw data that has not undergone the smoothing processing is used into a blood glucose level with a conversion factor of 0.00007 (mg/dL)−1, and when compared with the actual measured blood glucose level 105, it can be seen that the estimated blood glucose level continuously increases after 12:00 in the same manner as in the graph 104. After providing the glucose load at 12:00, a change corresponding to the change in the blood glucose level caused by the glucose load is significantly reduced compared with the graph 104.

Figure 35:
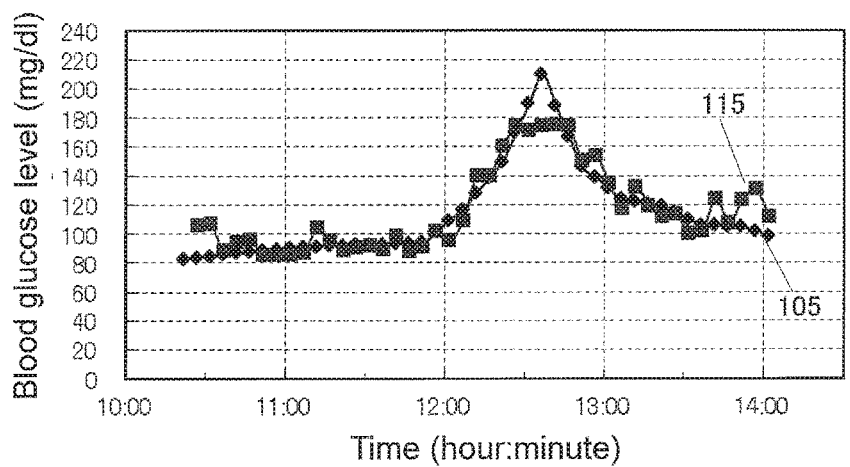
FIG. 35 is a diagram illustrating a change over time in an actual measured blood glucose level and a change over time in a corrected estimated blood glucose level.

FIG. 35 shows the relationship between the actual measured blood glucose level 105 and the estimated blood glucose level 115 in which the error is corrected by calculating the difference between the glucose concentration index (CG) and the error (CError) and matching the initial blood glucose level with 93 mg/dl, which is the actual measured blood glucose level at the start of the measurement. The correlation coefficient between the actual measured blood glucose level and the estimated blood glucose level was 0.93.

With the method of this embodiment, it is possible to correct the error caused by unknown disturbance components, and therefore, it is possible to accurately quantify the glucose concentration even in the case where the number of components in the measured spectrum is different from the number of components in the component spectrum to be used in the synthesis, resulting in the mixing of unknown disturbances, which is a disadvantage of the spectral synthesis method.

As described above, it is possible to simply and accurately quantify the concentrations of the components in a living organism, particularly the glucose concentration, by synthesizing the difference spectrum and correcting the amount of the errors.

Figure 36:
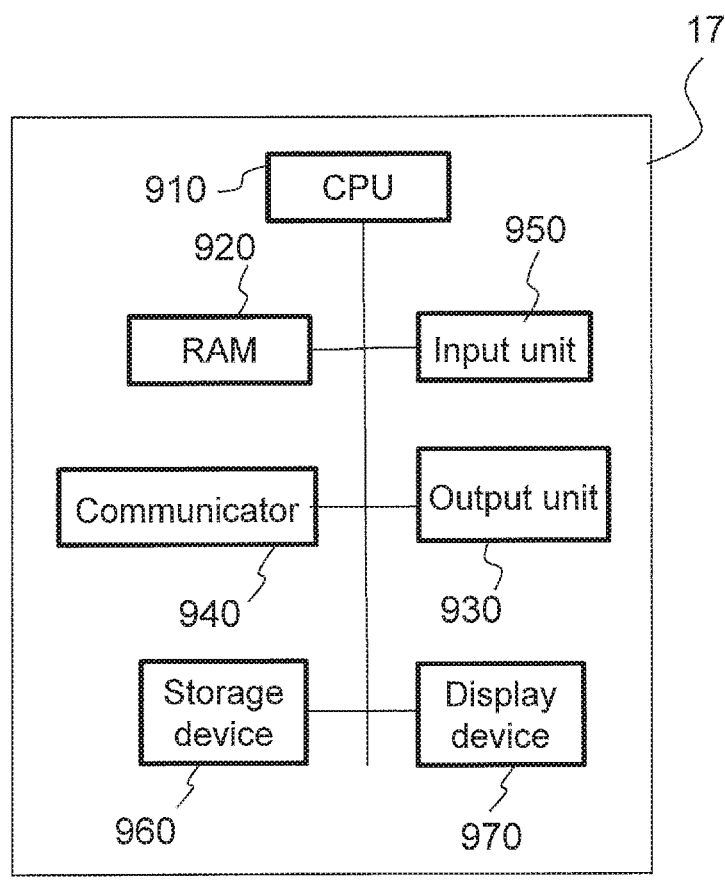
FIG. 36 is a diagram illustrating an example of a hardware configuration of an arithmetic device of a glucose concentration measurement device of an embodiment according to an implementation of the present invention.

It should be noted that the arithmetic device 17 of Embodiments 1 to 5 described above may be implemented using a hardware configuration shown in FIG. 36. The arithmetic device 17 is configured by a personal computer, portable computer terminal, or the like, and includes a CPU (central processing unit) 910, a RAM (random access memory) 920, an output unit 930, a communicator 940, an input unit 950, a display device 970, a storage device 960, and the like, for example.

The communicator 940 constitutes the spectral data receiving unit 201, for example, and receives spectral data.

The CPU 910 executes various arithmetic processing and the like, and a predetermined control program that is loaded into the RAM 920 and developed. This control program is used to execute the functions of the constituents such as the difference spectrum producing unit 202, the normalizing unit 203, the first imaginary spectrum producing unit 204, the second imaginary spectrum producing unit 205, the concentration index calculation unit 206, the error concentration index calculation unit 207, the correcting unit 208, and the glucose concentration calculation unit 209. The RAM 920 is configured by a memory element such as an SRAM and a DRAM, and data and the like generated during the processes performed by the CPU 910 are stored in the RAM 920.

The output unit 930 has a connection terminal to which a cable that transmits an analogue signal or digital signal of an image, sound, and the like is connected. The output 930 converts various information read from the storage device 960 into an image signal in accordance with an instruction from the CPU 910, and outputs the image signal to the display device 970 and the like through the cable. The display device 970 displays the measured glucose concentration and the like, for example.

The input unit 950 is configured by a mouse, a keyboard, a touch panel that enables operations on the screen, and the like. The input unit 950 receives information inputted and menu selected by the operation of a user and sends the received operation contents to the CPU 910.

The storage device 960 is configured by a semiconductor memory, a magnetic recording medium, an optical recording medium, or the like. The storage device 960 constitutes the storage unit 210, for example, and the conversion factor to be used to convert a concentration index CG value into a change in the glucose concentration, the spectral data at the time of the measurement of a glucose concentration, the reference spectral data, the difference spectrum, the difference spectrum normalized at 1400 nm, the first imaginary spectrum data, the second imaginary spectrum data, the spectral data of the water component, the spectral data of the protein (collagen) component, the spectral data of the glucose component, and the like are stored in the storage device 960.

In the above-mentioned embodiments, when the blood glucose level is quantified, the glucose concentration at the time of the measurement of a reference spectrum is matched with the actual measured blood glucose level at that time. However, there is no need of matching with the blood glucose level, and matching with the glucose concentration in the intercellular fluid may be performed so that the glucose concentration in the intercellular fluid may be quantified.

INDUSTRIAL APPLICABILITY

As described above, certain implementations of the present invention enable the concentration of a minor component, particularly glucose, in a living organism to be continuously measured accurately and noninvasively. Furthermore, several wavelengths can be selected as the measurement wavelength, and therefore, it is possible to simplify the computation for the calculation of the glucose concentration and to reduce the size of the device.

That is, it is expected that certain implementations of the present invention will be widely used as a glucose concentration measurement device for managing diabetic patients in which the glucose concentration is required to be continuously measured and patients in an ICU (intensive care unit) or an operation room.

The invention claimed is:

1. A method for quantifying a glucose concentration in which near-infrared light is emitted onto a living organism and the glucose concentration in a biological tissue is measured using a signal obtained by receiving diffusely reflected light or transmitted light from the biological tissue, the method comprising:
 a first imaginary spectrum producing step of producing a first imaginary spectrum determined, in each measurement in a measurement spectrum at a time of measurement of the glucose concentration, by adding together a characteristic wavelength of a baseline variation and a characteristic wavelength of a spectrum of a fat component,
 a concentration index calculation step of calculating a concentration index of a glucose component by using at least a spectrum of a water component, a spectrum of the glucose component, and the first imaginary spectrum to synthesize a difference spectrum between a measurement spectrum at the time of measurement of the glucose concentration and a spectrum serving as a reference obtained prior to the measurement spectrum; and
 a glucose concentration calculation step of calculating the glucose concentration in the living organism using the calculated concentration index.

2. The method for quantifying a glucose concentration according to claim 1,
 wherein, in the concentration index calculation step, the concentration index of the glucose component is calculated by using at least three absorption signals that are:
 an absorption signal at a first characteristic wavelength selected from 1450±30 nm, which is a characteristic wavelength range of the water component, as an index indicating the spectrum of the water component;
 an absorption signal at a second characteristic wavelength selected from 1600±30 nm, which is a characteristic wavelength range of the glucose component, as an index indicating the spectrum of the glucose component; and
 an absorption signal at a third characteristic wavelength selected from 1727±30 nm, which is a characteristic wavelength range of the fat component, as an index indicating the first imaginary spectrum.

3. The method for quantifying a glucose concentration according to claim 2,
 wherein, in the concentration index calculation step, a square matrix is produced using:
 absorption signals of the spectrum of the water component, the spectrum of the glucose component, and the first imaginary spectrum at the first characteristic wavelength;
 absorption signals of the spectrum of the water component, the spectrum of the glucose component, and the first imaginary spectrum at the second characteristic wavelength; and
 absorption signals of the spectrum of the water component, the spectrum of the glucose component, and the first imaginary spectrum at the third characteristic wavelength, and
 the concentration index of the glucose component is calculated using an inverse matrix of the square matrix.

4. The method for quantifying a glucose concentration according to claim 1,
 wherein, in the first imaginary spectrum producing step, the characteristic wavelength of the spectrum of the fat component is selected from a wavelength range of 1727±30 nm, and the characteristic wavelength of the baseline variation is selected from a wavelength range of 1650±30 nm.

5. The method for quantifying a glucose concentration according to claim 1,
 wherein, in the first imaginary spectrum producing step, the first imaginary spectrum is produced based on, in the measurement spectrum at the time of the measurement of the glucose concentration, the characteristic wavelength of the baseline variation and the characteristic wavelength of the spectrum of the fat component, which have undergone smoothing processing.

6. The method for quantifying a glucose concentration according to claim 1,
 wherein the measurement spectrum or the difference spectrum, the spectrum of the water component, the spectrum of the glucose component, and the first imaginary spectrum are normalized at a wavelength selected from 1400±20 nm.

7. The method for quantifying a glucose concentration according to claim 5, further comprising:
 a second imaginary spectrum producing step of producing a second imaginary spectrum based on, in the measurement spectrum, the characteristic wavelength of the baseline variation and the characteristic wavelength of the spectrum of the fat component, which have not undergone the smoothing processing;
 an error concentration index calculation step of calculating an error concentration index by using at least the spectrum of the water component, the spectrum of the glucose component, and the second imaginary spectrum to synthesize the difference spectrum; and
 a correcting step of correcting the calculated concentration index using the corrected calculated error concentration index,
 wherein, in the glucose concentration calculation step, the glucose concentration in a living organism is calculated using a corrected concentration index.

8. The method for quantifying a glucose concentration according to claim 7, wherein, in the second imaginary spectrum producing step, the characteristic wavelength of the spectrum of the fat component is selected from a wavelength range of 1727±30 nm, and the characteristic wavelength of the baseline variation is selected from a wavelength range of 1650±30 nm.

9. The method for quantifying a glucose concentration according to claim 7,
 wherein the measurement spectrum or the difference spectrum, the spectrum of the water component, the spectrum of the glucose component, the first imaginary spectrum, and the second imaginary spectrum are normalized at a wavelength selected from 1400±20 nm.

10. The method for quantifying a glucose concentration according to claim 7,
wherein, in the correcting step, a correction using the error concentration index is performed by subtracting the calculated error concentration index from the calculated concentration index of the glucose component.

11. The method for quantifying a glucose concentration according to claim 7,
wherein, in the concentration index calculation step, a concentration index of a glucose component is calculated by using the spectrum of the water component, the spectrum of the glucose component, the first imaginary spectrum, and a spectrum of a protein component to synthesize a difference spectrum between the measurement spectrum and a spectrum serving as a reference obtained prior to the measurement spectrum, and
in the error concentration index calculation step, an error concentration index is calculated by using at least the spectrum of the water component, the spectrum of the glucose component, the second imaginary spectrum, and the spectrum of the protein component to synthesize the difference spectrum.

12. A glucose concentration measurement device, comprising:
a light source emitting near-infrared light;
a light receiving unit receiving light that has been emitted onto a surface of a living organism by the light source and that is transmitted or reflected by the living organism and then subjected to spectroscopy;
a first imaginary spectrum producing unit producing a first imaginary spectrum determined, in each measurement in a measurement spectrum at a time of measurement of a glucose concentration, by adding together a characteristic wavelength of a baseline variation and a characteristic wavelength of a spectrum of a fat component,
a concentration index calculation unit calculating a concentration index of a glucose component by using at least a spectrum of a water component, a spectrum of the glucose component, and the first imaginary spectrum to synthesize a difference spectrum between a measurement spectrum at the time of measurement of the glucose concentration and a spectrum serving as a reference obtained prior to the measurement spectrum; and
a glucose concentration calculation unit calculating the glucose concentration in the living organism using the calculated concentration index.

13. The glucose concentration measurement device according to claim 12, further comprising:
a first imaginary spectrum producing unit producing a first imaginary spectrum based on, in a measurement spectrum at the time of measurement of the glucose concentration, a characteristic wavelength of a baseline variation and a characteristic wavelength of the spectrum of the fat component, which have undergone smoothing processing,
wherein the concentration index calculation unit calculates the concentration index of the glucose component using the first imaginary spectrum instead of the spectrum of the fat component.

14. The glucose concentration measurement device according to claim 13, further comprising:
a second imaginary spectrum producing unit producing a second imaginary spectrum based on, in the measurement spectrum, the characteristic wavelength of the baseline variation and the characteristic wavelength of the spectrum of the fat component, which have not undergone the smoothing processing;
an error concentration index calculation uncalculating an error concentration index by using at least the spectrum of the water component, the spectrum of the glucose component, and the second imaginary spectrum to synthesize the difference spectrum; and
a correcting unit correcting the calculated concentration index using the corrected calculated error concentration index,
wherein the glucose concentration calculation unit calculates the glucose concentration in a living organism using the corrected concentration index.

* * * * *